(12) United States Patent
Draper et al.

(10) Patent No.: US 6,841,720 B1
(45) Date of Patent: Jan. 11, 2005

(54) INDUCIBLE PROMOTERS

(75) Inventors: John Draper, Aberystwyth (GB); Paul Kenton, Aberystwyth (GB); Robert Darby, Aberystwyth (GB); Wyatt Paul, Cambridge (GB)

(73) Assignee: Biogemma UK LTD (GB)

( * ) Notice: Subject to any disclaimer, the term of this patent is extended or adjusted under 35 U.S.C. 154(b) by 0 days.

(21) Appl. No.: 09/719,002

(22) PCT Filed: Jun. 21, 1999

(86) PCT No.: PCT/GB99/01949
§ 371 (c)(1),
(2), (4) Date: Aug. 1, 2001

(87) PCT Pub. No.: WO99/66057
PCT Pub. Date: Dec. 23, 1999

(30) Foreign Application Priority Data

Jun. 19, 1998 (GB) .............................................. 9813345

(51) Int. Cl.⁷ ........................... C12N 15/82; A01H 5/00
(52) U.S. Cl. ................. 800/287; 435/252.3; 435/320.1; 435/419; 435/468; 536/24.1
(58) Field of Search ........................... 435/252.3, 320.1, 435/419, 468; 536/24.1; 800/287, 298

(56) References Cited

FOREIGN PATENT DOCUMENTS

| EP | 0 332 104 | 9/1989 |
|----|-----------|--------|
| WO | WO 93/05164 | 3/1993 |
| WO | WO 98/03536 | 1/1998 |

OTHER PUBLICATIONS

Hennig et al. Pathogen, salicylic acid and developmental dependent expression of a beta–1,3–glucanase/GUS gene fusion in transgenic tobacco plants. Plant J. Sep. 1993;4(3):481–93.*

Menke et al. A novel jasmonate– and elicitor–responsive element in the periwinkle secondary metabolite biosynthetic gene Str interacts with a jasmonate– and elicitor–inducible AP2–domain transcription factorThe EMBO Journal, 1999, 18(16):4455–4463.*

Shah et al. Identification of a salicylic acid–responsive element in the promoter of the tobacco pathogenesis–related B–1,3–glucanase gene, PR–2d. The Plant Journal, 1996, vol. 10, No. 6, pp. 1089–1101.*

Görlach, J., et al., "Benzothiadiazole, A Novel Class of Inducers of Systemic Acquired Resistance, Activates Gene Expression and Disease Resistance in Wheat," *The Plant Cell* 8:629–643, American Society of Plant Physiologists (1996).

International Search Report for Application No. PCT/GB99/01949, mailed Dec. 1999.

* cited by examiner

*Primary Examiner*—David T. Fox
*Assistant Examiner*—Cynthia Collins
(74) *Attorney, Agent, or Firm*—Sterne, Kessler, Goldstein & Fox P.L.L.C.

(57) ABSTRACT

The present invention relates to inductible promoters for use in the control of heterologous genes in transformed plants. Suitable inducible promoters art those which are responsive to low levels of an environmentally acceptable and non-phytoxic inducing agent, and which also demonstrates a low level of developmentally or environmentally induced expression. A preferred prompter naturally drives the expression of a 21.3 kDa protein in *Asparagus officinalis* or an equivalent protein from the Lillaceae or Amaryllidaceae families. Under the control of a promoter of the invention, a gene will be expressed upon induction by SA or BTH, but preferably will not be developmentally expressed, systemically activated upon pathogen infection, or in response to ABA, ethylene, oxidative or osmotic stresses, or wounding.

17 Claims, 18 Drawing Sheets

FIG. 1 – AoPRT-L cDNA sequence

```
         10         20         30         40         50         60         70
         |          |          |          |          |          |          |
ATGGCTCTATCCAAAGCTTCACCTCCCTCCCTCCTGCTCCTGTCCTCCTGCCCCTCGCCTCCGCCGCCACCTTC
 M  A  L  S  K  A  F  T  S  L  L  L  P  V  L  L  L  P  L  A  S  A  A  T  F 80         90        100        110        120        130        140        150
         |          |          |          |          |          |          |          |
                                                                     cgcctgcagccaa
< P1 ccaacaaatgcacctacacccgaattccgcg
ACCGTCACCAACAAATGCACCTACACCGTCTGGGCCGCTGCAGTGCCGGGGGGCCGGCGTCGCCGCCTCGACCCAACCAA
 T  V  T  N  K  C  T  Y  T  V  W  A  A  A  V  P  G  G  G  R  R  L  D  P  N  Q 160        170        180        190        200        210        220        230
         |          |          |          |          |          |          |          |
tcctggaccctcaccg  >P2
TCCTGGACCCTCACCGTCGCCCCCGGTACCACCGGTGCCCGCATCTGGGGCCGAACCGGTTGCTCCTTCGACCCCTCT
 S  W  T  L  T  V  A  P  G  T  T  G  A  R  I  W  G  R  T  G  C  S  F  D  P  S 240        250        260        270        280        290        300        310
         |          |          |          |          |          |          |          |
GGCCACGGCCATTGCCAGACGGGTGACTGCGGGGGTCTCCTTGCCTACGGCTCCCCTCCCGACACCCTC
 G  H  G  H  C  Q  T  G  D  C  G  G  L  L  A  C  T  A  Y  G  S  P  P  D  T  L
```

```
GCAGAATTCGCCCTGAACCAGTACGCCGGCCAGGACTTCTACGACATCTCCCTGTCGACGGCTTCAACATCCCCATG
  A  E  F  A  L  N  Q  Y  A  G  Q  D  F  Y  D  I  S  L  V  D  G  F  N  I  P  M

GACTTCTCCCCGACGTCCGGAAATTGCCACGACATCCGTGCACCGGGACATCAACGGTCAGTGCCCGGCGGAGCTG
 D  F  S  P  T  S  G  N  C  H  D  I  R  C  T  A  D  I  N  G  Q  C  P  A  E  L

AAGGCACCCGGGGGTGTAACACCCGTGCACCGTGTTCAAGACCAATGAGTACTGCTGCACTTCGGGAGCTGTGGG
 K  A  P  G  G  C  N  N  P  C  T  V  F  K  T  N  E  Y  C  C  T  S  G  G  G

CCCACGGACTATTCCAAGTTTTTCAAGCAGAGGTGCCCTGATGCGTACAGTTACCCCAAGGATGACGCTACCAGCACT
 P  T  D  Y  S  K  F  F  K  Q  R  C  P  D  A  Y  S  Y  P  K  D  D  A  T  S  T

TTTACTTGTCCCAGTGGGCTGATTACAGGGTGTGTTCTGCCCTTGATGAGCTTACTCAGATGTTGTGTGAGCAAT
 F  T  C  P  S  G  A  D  Y  R  V  V  F  C  P  *

CAAACTATGGTTAATTTGTACGTAGCTCATTAAGAACGAATAAGGTCGCATGTAAGCTCTACTTGAGC
```

Similarity of AoPRT-L to other PR-5 Group Proteins

| Protein | Cellular Location | pI | Similarity | Percentage Similarity or Identity to AoPRT-L |
|---|---|---|---|---|
| AoPRT-L | Extracellular | 4.9 | 100 | 100 |
| Osmotin | Vacuolar | 7.5 | 89 | 77 |
| Tobacco Osmotin-like | Vacuolar | 7.5 | 89 | 77 |
| Tobacco Thaumatin-like | Extracellular | 5.2 | 80 | 80 |
| Tomato NP24 | Vacuolar | 7.8 | 78 | 65 |
| Thaumatin | Cytoplasmic | 12.0 | 76 | 63 |
| Potato Osmotin-like | ? | 6.1 | 76 | 62 |
| Rice Thaumatin-like | ? | 5.0 | 70 | 53 |
| Wheat Thaumatin-like | Extracellular | 4.5 | 68 | 49 |
| Barley Thaumatin-like | Extracellular | 4.2 | 67 | 49 |

FIG.3a

Induction of AoPRT-L following cell isolation

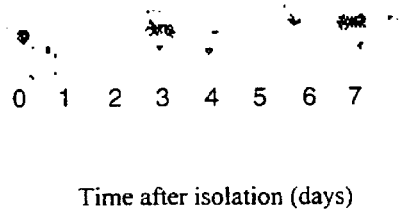

0  1  2  3  4  5  6  7

Time after isolation (days)

FIG.3b

Induction in etiolated seedlings by wounding

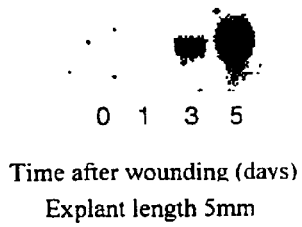

0  1  3  5

Time after wounding (days)
Explant length 5mm

FIG.3c

Induction of AoPRT-L in whole plants by SA    Time course of induction following foliar
application of 1mM SA to whole plants

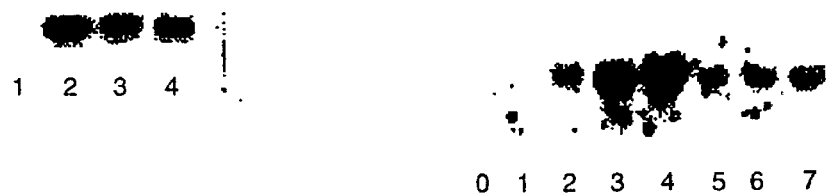

1  2  3  4                                    0  1  2  3  4  5  6  7

1; Water treated
2; 3 days after foliar spraying with 1mM SA
3; 3 days after continuous root feeding with 1mM SA                Time after application (days)
4; 3 days after initial root feeding with 1mM SA

FIG.4

**AoPRT-L Expression in Asparagus seedlings infected with *Stemphyllium versicarium***

3 . 7   14   C   M   P   A   — AoPRT-L

Figures (3, 7 & 14) indicate days after symptom development

C - uninfected Asparagus
M - Infected region (day 14)
P - Pigmented region (day 14)
A - Asymptomatic region (day 14)

FIG. 5
IPCR Strategy
Southern Analysis
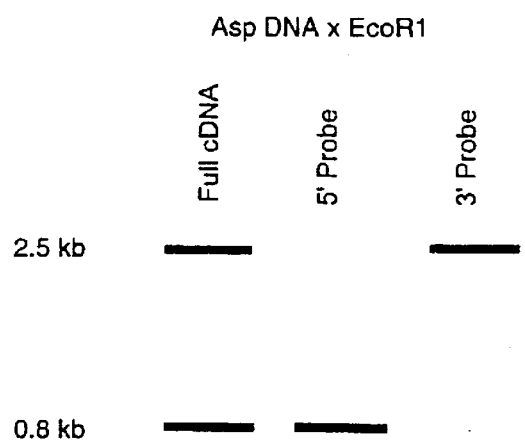
Primer Design
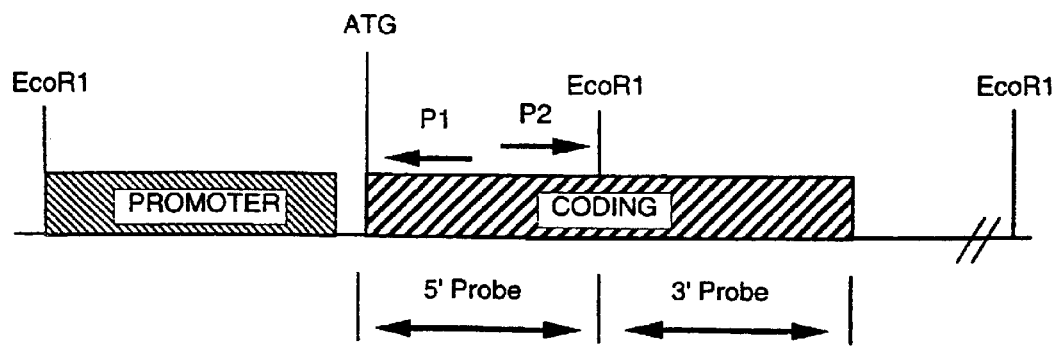

pIPCR-TA
PCR using 5' and 3' primers
Clone into pJIT60 using KpnI and PstI
p22-JIT60
Clone in GUS(INT) using BamHI and EcoRI
p22-GUS(INT) JIT60
Cut with KpnI and XhoI and clone into KpnI and SalI cut pBin19
p22-GUS(INT) Bin19
FIG. 7

Histochemical localistion of GUS activity in untreated stems from transgenic tobacco harbouring AoPRT-L-GUS or PR-1a-GUS AoPRT-L-GUS    PR-1a-GUS ← Internode ← Node

FIG. 9
AoPRT-L-GUS Expression in TMV-infected Tobacco
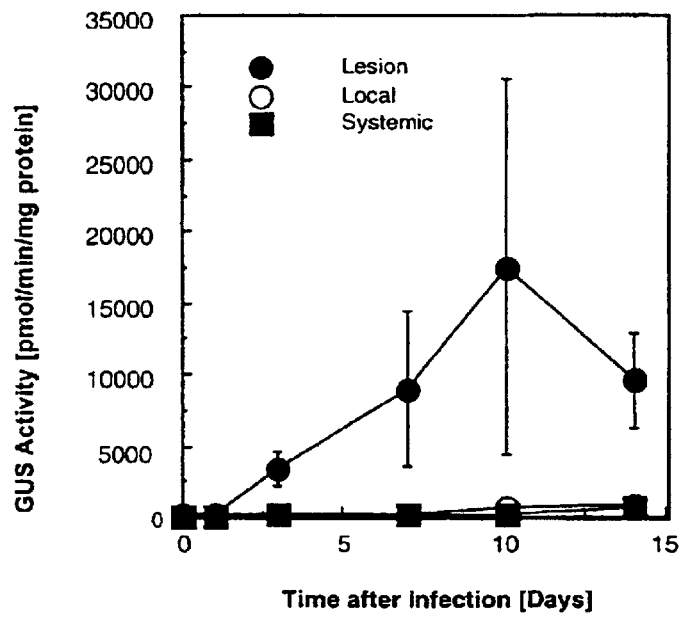
**AoPRT-L-GUS Expression in Tobacco infected with *Pseudomonas syringae* pathovar *phaseolicola***
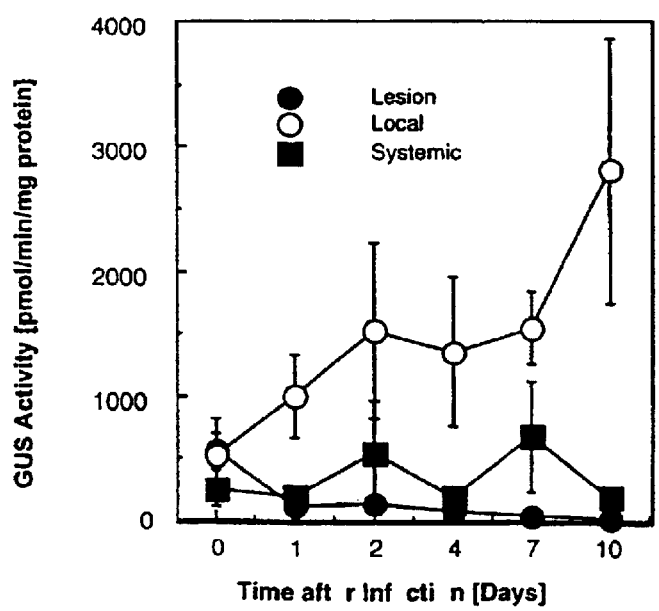

Effects of wounding and JA on GUS expression in transgenic plants

FIG. 13 AoPRT-L-GUS Expression following Oxidative Stress

AoPRT-L-GUS and Pr1a-Gus expression after SA or BTH induction in Brassica napus leaves FIG. 15a AoPRT-L promoter deletions
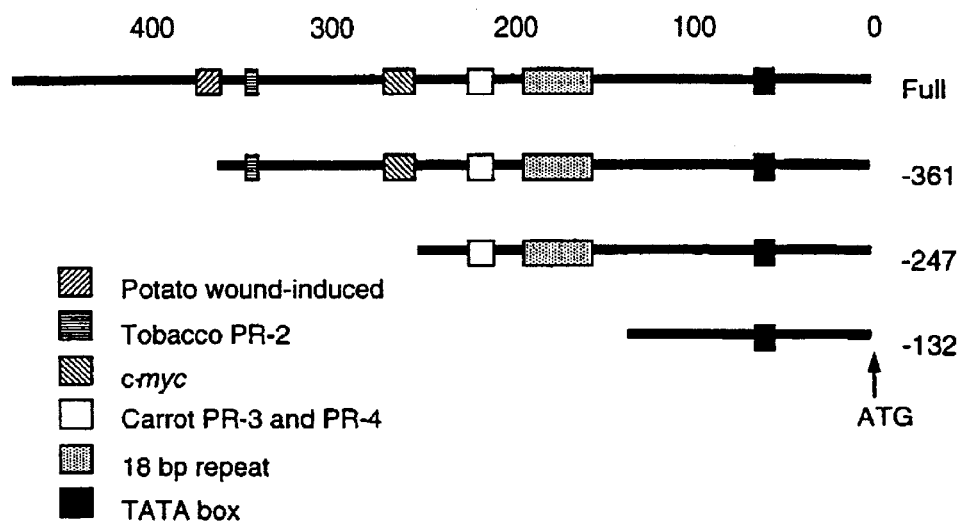
FIG. 15b SA-responsiveness of AoPRT-L promoter deletion-GUS constructs in T0 transgenic tobacco plants
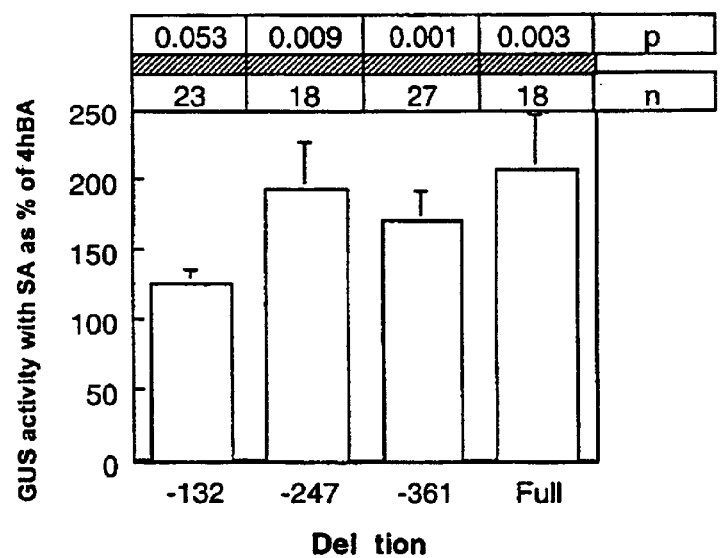
n - number of individual transformants
p - probability that activity with SA is not different to activity with control-treatment
(Wilcoxon signed rank test)

schematic diagram of plasmid pGB24

SEQUENCE LISTING

<160> NUMBER OF SEQ ID NOS: 19

<210> SEQ ID NO 1
<211> LENGTH: 475
<212> TYPE: DNA
<213> ORGANISM: Asparagus officinalis

<400> SEQUENCE: 1

```
gaattcttat tgcgacctga ctctcttgtt gtgctgccga ggtgctgtcg aaatttctgt      60
tgcgcacaac atactggtcc ttgcttgatt tgacagttcc aataattatt tccatgtcat     120
gagagaagca catgactaaa gtaattagct taatccccta aaactcaata caaacgagat     180
gacacatcca cagaaaaaat tctaattagt ctttgcgtgt agaaattgga aactgaatac     240
ctacattaat tacaactttt gcaaataaaa tataaagaaa gttctaacat gaagactagt     300
tctaacatga agactagtcc acgaactcgt accttattcc acaaaggctt agactttcca     360
caaatcgaga ttatcccatg gactgatgga caccatccaa attatcccta taaatacctg     420
cccattcccc tcctccagac tcatctaact caaaaacaac acacaaccaa tcatg          475
```

<210> SEQ ID NO 2
<211> LENGTH: 771
<212> TYPE: DNA
<213> ORGANISM: Asparagus officinalis
<220> FEATURE:
<221> NAME/KEY: CDS
<222> LOCATION: (1)..(672)

<400> SEQUENCE: 2

```
atg gct cta tcc aaa gct ttc acc tcc ctc ctc ctc ctc cct gtc ctc      48
Met Ala Leu Ser Lys Ala Phe Thr Ser Leu Leu Leu Leu Pro Val Leu
 1               5                  10                  15 ctc ctg ccc ctc gcc tcc gcc gcc acc ttc acc gtc acc aac aaa tgc      96
Leu Leu Pro Leu Ala Ser Ala Ala Thr Phe Thr Val Thr Asn Lys Cys
            20                  25                  30 acc tac acc gtc tgg gcc gct gca gtg ccg ggg ggc ggt cgc cgc ctc     144
Thr Tyr Thr Val Trp Ala Ala Ala Val Pro Gly Gly Gly Arg Arg Leu
        35                  40                  45 gac ccc aac caa tcc tgg acc ctc acc gtc gcc ccc ggt acc acc ggt     192
Asp Pro Asn Gln Ser Trp Thr Leu Thr Val Ala Pro Gly Thr Thr Gly
    50                  55                  60 gcc cgc atc tgg ggc cga acc ggc tgc tcc ttc gac ccc tct ggc cac     240
Ala Arg Ile Trp Gly Arg Thr Gly Cys Ser Phe Asp Pro Ser Gly His
65                  70                  75                  80 ggc cat tgc cag acc ggt gac tgc ggc ggt ctc ctt gcc tgc acc gcc     288
Gly His Cys Gln Thr Gly Asp Cys Gly Gly Leu Leu Ala Cys Thr Ala
                85                  90                  95 tac ggc tcc cct ccc gac acc ctc gca gaa ttc gcc ctg aac cag tac     336
Tyr Gly Ser Pro Pro Asp Thr Leu Ala Glu Phe Ala Leu Asn Gln Tyr
            100                 105                 110
```

```
gcc ggc cag gac ttc tac gac atc tcc ctc gtc gac ggc ttc aac atc      384
Ala Gly Gln Asp Phe Tyr Asp Ile Ser Leu Val Asp Gly Phe Asn Ile
        115                 120                 125 ccc atg gac ttc tcc ccg acg tcc gga aat tgc cac gac atc cgg tgc      432
Pro Met Asp Phe Ser Pro Thr Ser Gly Asn Cys His Asp Ile Arg Cys
130                 135                 140 acc gcg gac atc aac ggt cag tgc ccg gcg gag ctg aag gca ccc ggg      480
Thr Ala Asp Ile Asn Gly Gln Cys Pro Ala Glu Leu Lys Ala Pro Gly
145                 150                 155                 160 ggg tgt aac aac ccg tgc acc gtg ttc aag acc aat gag tac tgc tgc      528
Gly Cys Asn Asn Pro Cys Thr Val Phe Lys Thr Asn Glu Tyr Cys Cys
                165                 170                 175 act tcg gga ggc tgt ggg ccc acg gac tat tcc aag ttt ttc aag cag      576
Thr Ser Gly Gly Cys Gly Pro Thr Asp Tyr Ser Lys Phe Phe Lys Gln
            180                 185                 190 agg tgc cct gat gcg tac agt tac ccc aag gat gac gct acc agc act      624
Arg Cys Pro Asp Ala Tyr Ser Tyr Pro Lys Asp Asp Ala Thr Ser Thr
        195                 200                 205 ttt act tgt ccc agt ggg gct gat tac agg gtt gtg ttc tgc cct tga      672
Phe Thr Cys Pro Ser Gly Ala Asp Tyr Arg Val Val Phe Cys Pro
    210                 215                 220 tcgagcttac tcagatgttg tgtgagcaat caaactatgg ttaatttgta cgtagctcat    732
taagaacgga ataaggtcgc atgtaagctc tacttgagc                           771

<210> SEQ ID NO 3
<211> LENGTH: 223
<212> TYPE: PRT
<213> ORGANISM: Asparagus officinalis

<400> SEQUENCE: 3

Met Ala Leu Ser Lys Ala Phe Thr Ser Leu Leu Leu Pro Val Leu
 1               5                  10                  15

Leu Leu Pro Leu Ala Ser Ala Ala Thr Phe Thr Val Thr Asn Lys Cys
            20                  25                  30

Thr Tyr Thr Val Trp Ala Ala Ala Val Pro Gly Gly Gly Arg Arg Leu
        35                  40                  45

Asp Pro Asn Gln Ser Trp Thr Leu Thr Val Ala Pro Gly Thr Thr Gly
    50                  55                  60

Ala Arg Ile Trp Gly Arg Thr Gly Cys Ser Phe Asp Pro Ser Gly His
65                  70                  75                  80

Gly His Cys Gln Thr Gly Asp Cys Gly Gly Leu Leu Ala Cys Thr Ala
                85                  90                  95

Tyr Gly Ser Pro Pro Asp Thr Leu Ala Glu Phe Ala Leu Asn Gln Tyr
            100                 105                 110

Ala Gly Gln Asp Phe Tyr Asp Ile Ser Leu Val Asp Gly Phe Asn Ile
        115                 120                 125

Pro Met Asp Phe Ser Pro Thr Ser Gly Asn Cys His Asp Ile Arg Cys
    130                 135                 140

Thr Ala Asp Ile Asn Gly Gln Cys Pro Ala Glu Leu Lys Ala Pro Gly
145                 150                 155                 160

Gly Cys Asn Asn Pro Cys Thr Val Phe Lys Thr Asn Glu Tyr Cys Cys
                165                 170                 175

Thr Ser Gly Gly Cys Gly Pro Thr Asp Tyr Ser Lys Phe Phe Lys Gln
            180                 185                 190

Arg Cys Pro Asp Ala Tyr Ser Tyr Pro Lys Asp Asp Ala Thr Ser Thr
        195                 200                 205
```

```
Phe Thr Cys Pro Ser Gly Ala Asp Tyr Arg Val Val Phe Cys Pro
    210                 215                 220
```

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4
ccaacaaatg cacctacacc gaattccgcg                              30

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: E-8

<400> SEQUENCE: 5
ataaggggtt ggt                                                13

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: JA Box

<400> SEQUENCE: 6
ccctataggg                                                    10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: TCA

<400> SEQUENCE: 7
ttatctcctt                                                    10

<210> SEQ ID NO 8
<211> LENGTH: 10
<212> TYPE: DNA
<213> ORGANISM: Hordeum vulgare

<400> SEQUENCE: 8
tcatcttctt                                                    10

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
cgcggaattc ggtgtaggtg catttgttgg                              30

<210> SEQ ID NO 10
<211> LENGTH: 29
<212> TYPE: DNA
<213> ORGANISM: Artificial Sequence
<220> FEATURE:

-continued

<223> OTHER INFORMATION: Description of Artificial Sequence: Primer

<400> SEQUENCE: 10
cgcctgcagc caatcctgga ccctcaccg                               29

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 11
gggtaccaag cttcttattg cgacctgact ctc                          33

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 12
cgcggatccg tcgacctgca ggattggttg tgtgttgttt t                 41

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 13
gcgaagcttc catgtcatga gagaagcac                               29

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 14
gcgaagcttt tggaaactga atacctaca                               29

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 15
gcgaagctta caaaggctta gactttcca                               29

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 16
gggatccgtc gacctgcaga ttggttgtgt gttgttttttg                  40

-continued

```
<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 17
tctaggtacc ctttgcgtgg tcgacttgga aactgaatac ctac                44

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 18
tctaggtacc ctttgcgtgg tcgacttgga aactgaatac ctac                44

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 19
gaaagtctaa gcctcgaggg aataaggtac gagttcgtgg ac                  42
```

INDUCIBLE PROMOTERS

CROSS REFERENCE TO RELATED APPLICATIONS

The present application is the National Phase of International Application No. PCT/GB99/01949, filed Jun. 21, 1999, which was published in English.

BACKGROUND OF THE INVENTION

1. Field of the Invention

The present invention relates to novel inducible promoters derived from plants and their application in the controlled expression of heterologous genes.

2. Related Art

The aim of crop plant genetic engineering is to insert a gene (or genes) which alter a plant's characteristics without altering otherwise desirable elements of the genotype of the original plant. Thus, the genetic make-up of crop plants can be extended to include genes outside of the original genetic pool which are not accessible by traditional crop breeding techniques. One important aspect of such modification is the choice of promoter. Conceptually, identification and characterisation of promoters allows the possibility to construct chimeric genes in which a promoter from one gene can be used to drive the expression of a protein encoded by a separate gene under conditions and at sites within the plant specified by the promoter.

Promoters often contain elements which are recognised by inducible factors which regulate the temporal and tissue-specific expression of genes. These elements are typically short sequences and are found in promoters of many (if not all) genes which respond to the same signal. Thus, in plants, analysis of promoters of genes which are upregulated by the phytohormone abscisic acid have identified a common element CCACGTT within these promoters (Marcotte et al., *Plant Cell* 1 969–976 (1989) and Pla et al., *Plant Mol. Biol.* 21 259–266 (1993)). Similarly, promoters responsive to ethylene contain the PR box AGCCGCC (Broglie et al., *Plant Cell* 1 599–607 (1989) and Deickman et al., *Plant Physiol.* 100 2013–2017 (1992)). Furthermore, possession of a selection of such response elements may confer upon a promoter either the ability to drive gene expression in response to any one of several signals or to display synergistic enhancement of expression in response to several signals. Table 1 lists a number of consensus response element sequences identified in plants.

TABLE 1

Promotor Response Elements

| Name | Sequence | Sensitivity | |
|---|---|---|---|
| ABRE | CCACGTT | ABA | |
| DRE1 | TACCGACAT | Drought | |
| E-8 | ATAAGGGGTTGGT | | (SEQ ID NO:5) |
| G Box | GTGTCAC | | |
| H Box | GGTAGG | | |
| JA Box | CCCTATAGGG | JA? | (SEQ ID NO:6) |
| Myb | TGGTTA | | |
| Myc | CANNTG | | |
| PR Box | AGCCGCC | Ethylene | |
| TCA | TTATCTCCTT | | (SEQ ID NO:7) |

Thus, from the DNA sequence of promoters, it is possible to predict the circumstances under which a promoter will be expressed by looking for already identified response elements within its sequence. It is with such inducible promoters that the present application is concerned.

Previously the expression of foreign proteins in transgenic plants has been driven by a 'constitutive' promoter such as Cauliflower mosaic virus 35S (CaMV 35S). Use of such a promoter in a commercial application is limited where the promoter is being used to drive toxic protein synthesis, or proteins which impose a substantial metabolic burden on the plant. These problems can be overcome if expression of the target protein is under the control of an inducible promoter, either just prior to or just after harvesting.

Several plant derived promoters have been previously proposed as being suitable for chemically regulated transgene expression (Gatz, C (1997) *Annu. Rev. Plant Physiol. Plant. Mol. Biol.* 48, 89–108). Such promoters are inducible by safeners or elicitors or chemicals mediating wound responses or chemicals inducing systemic acquired resistance (SAR). Promoters induced by safeners or by chemicals that induce SAR have been most studied. For example WO 93/01294 and Jepson et al., (1994) *Plant Mol. Biol.* 26, 1855–1866, describe the isolation of a glutathione S-transferase gene (GST-27) inducible by the safener N,N-diallyl-2,2-dichloroacetimide. The applications of this promoter are however limited since the promoter is constitutively expressed in roots.

The phenomenon of systemic acquired resistance (SAR) following infection of a plant with pathogenic microorganisms has long been established. When a plant is invaded by a potential pathogen, which it is able to recognise, a resistance response is activated. This response, known as an incompatible interaction, typically involves hypersensitive cell death at the site of pathogen ingress, phytoalexin synthesis, the production of active oxygen species, cell wall strengthening, local induction of defence genes and salicylic acid (SA) accumulation. Following on from this local response, SAR is established throughout the plant. SAR endows uninfected tissue with the ability to respond more rapidly to further infection and this resistance is effective against a wide range of potential pathogens. The synthesis of a number of relatively unrelated proteins known as pathogenesis-related proteins (PR proteins) accompanies the onset and establishment of SAR.

It has long been known that treatment of plants with either SA or acetyl-SA (aspirin) can induce resistance to pathogens (White, R. F. (1979). *Virology* 99, 410–412). Recent research has demonstrated that SA plays a key role in both the local and systemic induction of PR proteins and the establishment of SAR (Malamy et al., (1990) *Science* 250, 1002–1004; Metraux et al., (1990) *Science* 250, 1004–1006; Yalpani et al., (1991): *Plant Cell* 3, 809–818). Furthermore, SAR and PR protein accumulation are compromised in plants that constitutively express a bacterial salicylate hydroxylase (which converts SA to catechol) further supporting a role for endogenous SA in these processes (Gaffney et al., (1993) *Science* 261, 754–756). Spraying, injection or root-feeding plants with SA strongly induces expression of PR gene promoters by 50–1000-fold over basal levels (e.g. Mur et al., (1996) *Plant J.* 9, 559–571). However, since the concentration of SA used in these studies (typically 1–2 mM) is phytotoxic, a great deal of effort has been put into identifying less harmful compounds capable of mimicking SA.

One compound in particular, BTH (benzo(1,2,3) thiadiazole-7-carbothoic acid S-methyl ester), is already marketed as a 'crop enhancer' and is available for large scale use in the field (Gorlach et al., (1996) *Plant Cell* 8, 629–643). An aqueous solution of 1.2 μM BTH is sufficient to induce PR gene expression (Friedrich et al., (1996) *Plant J.* 10, 61–70). Commercial preparations of BTH are sufficient to induce very strong PR gene expression in all plants tested including arabidopsis and wheat.

Gene induction following spraying with BTH is maximal 2 days after application and persists for at least 10 days. Although it induces enhanced resistance in treated tissue, its mode of action is unknown, nor is it known whether this compound can mimic all of SA's effects such as potentiation of gene induction or the pathogen-induced oxidative burst.

Thus, a potential source for inducible promoters is the pathogenesis-related (PR) 'family' of defence-related genes. PR genes are a diverse set of proteins some of which (e.g. PR-2 and PR-3 classes) have known functions as chitinases or beta-1,3-glucanase. Others (e.g. the PR-1 and PR-5 classes) are induced during plant-pathogen responses but have no clearly identifiable function. Typically, PR proteins of each class contain members with acidic or with basic pHs. Although there are exceptions to the rule, basic PR proteins tend to be localised to an intracellular site (e.g the vacuole) whilst acidic PR proteins are secreted.

Plants also have to respond to a variety of other environmental stresses including water stress, mechanical and herbivore wounding, UV light and oxidative stress, and both high and low temperatures. PR genes are upregulated in a number of these conditions. Thus, expression of tobacco osmotin (a basic, vacuolar PR-5 gene) is induced not only by pathogen challenge but also by salt stress (Grillo et al., *Physiologia Plantarum* 93 498–504 (1995)). PR-1a expression is induced following treatment with hydrogen peroxide (which induces oxidative stress) and in plants subjected to UV stress (Yalpani et al., *Planta* 193 372–376 (1994)). The responses to wounding and to pathogen challenge share a number of similar features including expression of defence genes and the establishment of a systemic response mediated by mobile signals. As a rule, basic PR proteins are also responsive to wounding stimuli.

A number of elements present in PR gene promoters have been identified. The PR-2d gene (encoding a β-1,3-glucanase) from tobacco is expressed in tissue undergoing hypersensitive response (HR) following tobacco mosaic virus (TMV) challenge and is induced by exogenous SA (Shah et al., *Plant J*. 10:1089–1101 (1996)). Region −364 to −288 in the PR-2d promoter confers SA sensitivity and a 25 bp element in this region is recognised by nuclear factors from tobacco. An SA responsive element has also been isolated from the CaMV 35S promoter at position −90 to −46. The element corresponds to an as-1 site (Qin et al., *Plant Cell* 6:863–874 (1994)). The sequence TCATCTTCTT (SEQ ID NO:8) is repeated several times in the barley β-1,3-glucanase promoter and is present in over 30 stress-induced genes (Goldsbrough et al., *Plant J*. 3(4):563–571 (1993b)). This region binds 40 kDa tobacco nuclear proteins, the binding of which is increased in SA-treated plants. Buttner et al., *Proc. Natl. Acad. Sci. USA* 94:5961–5966 (1997) have shown that Arabidopsis ethylene responsive element binding proteins bind to the PR box and that PR- and G-boxes exhibit synergistic effects.

PR-1 genes have been studied in some detail and the promoter of one, tobacco PR-1a, has been proposed as a suitable inducible promoter (EP 0 332 104 A2). Tobacco PR-1a is expressed both locally in infected tissue and later during establishment of SAR. Thus, infection of Samsun NN tobacco plants leads to accumulation of endogenous PR-1 proteins in both inoculated leaves (approx. 4 days after infection) and later (approx. 8 days) in upper uninfected leaves on the same plant. Local (approx. 12 hours post-inoculation) and systemic (3–7 days) induction of PR-1a-GUS expression in *Pseudomonas syringae* pathovar syringae-infected tobacco has been reported. (Bi et al., (1995) *Plant J*. 8:235–245; Mur et al., (1996) *Plant J*. 9:559–571). Direct application of SA induces high levels of PR-1a promoter-GUS expression in transgenic tobacco [Bi et al., supra]. The SAR inducers BTH and INA also induce high levels of both endogenous PR-1a and PR-1a-GUS expression.

Wounding also induces a slight increase in PR-1a-GUS expression (Darby, R., unpublished observations, Ohshima et al., (1990) *Plant Cell* 2, 95–106). As with other PR-1 proteins, PR-1a exhibits developmental expression. Thus, PR-1a-GUS is expressed in leaves, petioles, stem cortex, pollen and sepals of flowering tobacco (Uknes et al., *Plant Cell*, 5(2):159–169 (1993)). PR-1a-GUS is also expressed in roots (Kenton, P; unpublished observations).

The PR-1a promoter has been studied extensively. Van de Rhee and Bol (*Plant Mol. Biol.*, 21(3):451–461 (1993b)) identified four regulatory elements in the PR-1a promoter all of which were required for maximal activity and no single element of which was capable of conferring promoter activity. The PR-1a promoter contains a number of elements that bind GT-1-like and Myb1 transcription factors (Buchel et al., *Plant Mol. Biol.*, 30(3):493–504 (1996)). In addition, SA and active analogues induce expression not only of PR genes but also myb1.

The high level of sensitivity to SA shown by the PR-1a gene and the very high levels of PR-1α-GUS expression following SA treatment or infection could lead to inappropriate expression of any PR-1a promoter-gene fusion as a result of perturbation of endogenous SA levels (brought about, e.g., by a change in redok status). This may limit its usefulness in driving genes the products of which are either toxic at high levels or impose a substantial metabolic burden on the plant. Finally, PR-1 genes in general and PR-1a in particular show a high level of constitutive/developmental expression, especially during flowering. Again, this could lead to a high degree of unscheduled expression of PR-1a promoter-driven transgenes.

PR-5 proteins are another class of PR proteins, and can be divided into two groups, the acidic extracellular thaumatin-like proteins and the basic intracellular osmotins. Classically osmotins have been associated with abiotic stresses. However, this osmotically-induced expression is typically additional to a high degree of constitutive (Stintzi et al., *Biochimie*, 75:687–706 (1993); Leone et al., *Plant Physiol.*, 106:703–712 (1994); Van Kan et al., *Plant Mol. Biol.*, 27:1205–1213 (1995)) and developmental expression (Linthorst, *Crit. Rev. Plant Sci.*, 10:123–150 (1991); Stintzi et al., *Physiol. Mol. Plant Pathol.* 38 137–146 (1991); Raghothama et al., *Plant Mol. Biol.* 34:393–402 (1997)). Osmotin expression is also elevated in response to stresses such as desiccation, wounding, low temperature (Raghothama et al., *Plant Mol. Biol.* 23:1117–1128 (1993); Grillo et al., (1995) supra; Zhu et al., *Plant Mol. Biol.*, 28:17–26 (1995b)), and chemical factors such as ethylene (in tobacco Raghothama et al., 1993, supra; Chang et al., *Physiologia-Plantarum*, 100:341–352 (1997)), and cytokinins (Thomas & Bohnert, *Plant Physiol.*, 103:1299–1304 (1993)). Pathogen challenge also induces osmotin expression (Zhu et al., *Plant Physiol.*, 108:929–937 (1995a); (1995b), supra; Chang et al., (1997), supra) which may be systemic for some osmotins (Zhu et al., (1995b), supra) or local for others (Zhu et al., (1995a), supra). Thus the osmotin genes do not appear to be ideal sources of inducible promoters.

Unlike the vacuolar-localised osmotins, acidic PR-5s (aPR-5) are secreted and lack the C-terminal extension which may be a vacuolar targeting signal (Linthorst, (1991), supra; Stintzi et al., (1993), supra). aPR5 proteins have been shown to be accumulated on pathogen attack, for example in barley (Bryngelsson & Green, *Plant Mol. Plant Path.*, 35:45–52 (1989); Boyd et al., *Plant Mol. Plant Path.*, 45:47–58 (1994);Reiss & Bryngelsson, *Physiol. Mol. Plant Path.*, 43:331–341 (1996);Schweizer et al., *Plant Physiol.*, 114:73–88 (1997);Vale et al., *Physiol. Mol. Plant Path.*, 44:207–215 (1994)) and wheat (Rebmann et al., *Plant Mol. Biol.*, 17:283–285 (1991)). Using western blots, Stintzi et al., (1991) were unable to detect aPR-5 in healthy tobacco leaves whereas osmotin was constitutively expressed. Following challenge with TMV, aPR-5 appears after 4–6 hours, whereas osmotin begins to accumulate over basal levels 2–4 hours post-inoculation (Stintzi et al., 1991). aPR-5 has been localised to extracellular pocket-like structures between mesophyll cells close to the infection site in TMV-infected tobacco (Dore et al., *Arch. Virol.*, 120:97–107 (1991)).

A number of other treatments have been shown to induce expression of extracellular aPR-5 proteins. Sunflower extracellular aPR-5 proteins are induced in leaf discs by 5 mM aspirin, 10 mM ethephon, 10 mM NAA, 10 mM 2,4 D, UV light, 5 mM MnCl2, 5 mM HgCl3, 5 mM citric acid and 5 mM oxalic acid (Jung et al., *Journal of Plant Physiol.*, 145:153–160 (1995)). 1 ppm INA induces expression of a barley homologue of rice thaumatin-like protein and JA that of a barley aPR5 (Schweizer et al., (1997), supra). aPR-5s are also expressed in cold-acclimated winter rye where they may play a role in preventing ice damage (Hon et al., *Plant Physiol.*, 109:879–889 (1995)).

However, information concerning developmental expression of aPR-5s is limited. In maize constitutive expression is mainly confined to non-embryonic tissues of the developing seed peaking two to four weeks after pollination but still detectable in desiccated seed. Only slight expression was detectable in maize leaves (Malehorn et al., *Plant Physiol.*, 106:1471–1481 (1994)). A 29 kDa thaumatin-like protein has been detected in ripe cherry fruits (Fils-Lycaon et al., *Plant Physiol.*, 111:269–273 (1996)).

Little is known about aPR-5 promoters since only a tobacco aPR5 promoter from the E2 gene has been isolated, fused to the reporter gene GUS and analysed (Albrecht et al., (1992) *Plant Mol Biol.* 18, 155–158). This study showed that TMV induced both local and systemic GUS activity; the local response being greater than the systemic response. The element(s) responsible for this TMV induction of this aPR-5 were found to lie in the −1364 to −718 promoter region. By nucleic acid hybridisation no significant homology was found between this tobacco PR-5 promoter and the PR-1a promoter.

BRIEF SUMMARY OF THE INVENTION

The present invention is based on the discovery of novel and useful inducible promoters which overcome some or all of the problems associated with the prior art by providing an inducible promoter which is responsive to low levels of an environmentally-acceptable and non-phytotoxic inducing agent capable of use in both field and in vitro conditions, and which also exhibits a low level of environmentally- or developmentally-induced expression, and low levels of pathogen induced systemic activation, when compared with similar promoters.

DETAILED DESCRIPTION OF THE INVENTION

Thus, in a first aspect of the present invention there is provided a recombinant or isolated DNA molecule comprising an inducible gene promoter which:

i) naturally drives the expression of a 21.3 kDa protein in *Asparagus officinalis* upon induction by plant regulators; or ii) naturally drives the expression of proteins equivalent to the 21.3 kDa protein of *Asparagus officinalis*, from the Lillaceae or Amaryllidaceae families; or iii) naturally drives the expression of proteins substantially homologous to those of i) or ii); or iv) hybridises under stringent conditions to any one of the promoters of i), ii) or iii).

The promoter defined in i) is derived from an *Asparagus officinalis* thaumatin-like PR-5-related gene (AoPRT-L) and is able to drive expression of heterologous genes in dicots and monocots. pAoPRT-L has several advantages over the use of previously described promoters in the expression of heterologous genes. Table 2 compares the characteristics of the AoPRT-L promoter with that of PR1a and osmotin.

TABLE 2

Comparative Expression Patterns of PR-1a, Osmotin and AoPRT-L

| Treatment | Site | PR-1a | Osmotin | AoPRT-L |
| --- | --- | --- | --- | --- |
| None | Leaves | + (flowering) | + | − |
| | Stem | + (vasculature +) (leaf axil) | + | + (leaf axil) |
| | Petiole | + (flowering) | ? | + (leaf axil) |
| | Roots | + | + | +/− |
| | Flowers | + (sepal + pollen) | ? | + (sepal tip) |
| Pathogen | HR lesion | + | ? | + (TMV) |
| | Local | + | + | + |
| | Systemic | + | +/− | − |
| BTH | | + | ? | + |
| INA | | + | + | + |
| Wound | | +/− | + | − |

From this data, and data in the Examples, it can be seen that:

1) pAoPRT-L exhibits minimal developmentally-regulated expression.

2) pAoPRT-L, unlike tobacco pPR1a and aPR5-E2, is not systemically activated by pathogen infection.

3) pAoPRT-L is not responsive to ABA, ethylene, oxidative and osmotic stresses and wounding.

4) pAoPRT-L expression is induced by SA and by BTH (Novartis) a chemical that is licensed for field use.

These characteristics make the pAoPRT-L promoter a favourable candidate for use in expression of foreign proteins in transgenic plants. In addition, suitable promoters as defined in ii) or iii) may also be identified which drive the expression of pathogenesis related proteins equivalent or homologous to the pAoPRT-L protein of *Asparagus officinalis* in the Lillaceae or Amaryllidaceae family or indeed in other plant families.

Proteins substantially homologous to the AoPRT-L protein of *Asparagus officinalis* or equivalent proteins from the Lillaceae or Amaryllidaceae families may be readily identified by a person skilled in the art using techniques known in the art, for example as described herein. Such proteins are those which are functionally equivalent to the AoPRT-L protein. Thus, substantially homologous proteins are preferably inducible pathogenesis related proteins which are substantially free of systemically activated expression and developmentally regulated expression.

An important advantage of the inducible promoters of the present invention is the lack of developmentally regulated and systemically activated expression. This is in contrast to the constitutive promoters usually used to drive expression of heterologous genes in transgenic plants, or the inducible promoters which also become activated in a developmental manner, or throughout the plant as a result of pathogen invasion. The use of an inducible promoter which is not developmentally or systemically activated is particularly useful in the production of transgenic gene products from plants in field conditions, as it allows the controlled harvesting of the desired product. A promoter which is not developmentally regulated will allow the expression of genes whose products may be harmful to, or reduce the fitness of the plant. If such products were expressed constitutively either in the entire plant or in a significant portion of the plant, or at key stages of development, the plant may suffer, develop abnormally or die. For example, promoters such as GST27 and PR1a have significant developmental expression which limits the range of transgenes that can be expressed using these promoters. However, where an inducible promoter of the present invention is used, any gene may be expressed because the risk of gene expression at inappropriate stages of development is avoided. The use of a promoter of the present invention which is further not systemically activated in response to pathogen invasion also broadens the spectrum of genes which may be expressed from the promoter because inappropriate expression, which may be harmful to the plant, is avoided in field conditions where plants are highly susceptible to pathogen attack. In summary, and as a result also of the lack of activation in response to stimuli such as oxidative and osmotic stresses, ABA, ethylene and wounding, the AoPRT-L promoter offers improved controllability of expression over currently existing plant derived promoters which are used or will potentially be used for chemically induced transgene expression. The inducibility of the promoter with a chemical accepted for field use further emphasises the suitability of the AoPRT-L promoter for expression of heterologous genes in field plants.

Pathogenesis related proteins, or PR proteins, may for the purpose of the present invention, be defined as those proteins which are expressed in plants reacting to pathogens. Hypersensitivity to a pathogen is characterized by a local response which includes necrosis of tissues immediately surrounding the infected site. Other features of a local hypersensitive response include phytoalexin synthesis, production of active oxygen species, cell wall strengthening, local induction of defence genes and accumulation of salicylic acid. This is in contrast to a sensitive response in which the pathogen spreads throughout the whole plant. The hypersensitive local response may be followed by the induction of systemic acquired resistance (SAR). This allows uninfected tissues to respond quickly upon re-invasion of a pathogen. Pathogenesis related proteins may be expressed during the hypersensitive response, and upon the onset of SAR. Examples of pathogens which may result in the expression of one or more of the pathogenesis related proteins include viruses or viroids, for example tobacco or cucumber mosaic virus, ringspot virus, necrosis virus, pelargonium leaf curl virus, red clover mottle virus and other similar viruses, fungi, for example, *Phythopophthora parasitica* or *Peronospora tabacina*, bacteria such as *Pseudomonas syringae*, or *Pseudomonas tabaci*, or aphids such as *Mycus persicae*. It should be understood that this is not an exhaustive list, and the hypersensitive response and SAR may be induced by a number of other pathogens not listed here.

A pathogenesis related protein may be identified by any number of known techniques. For example, a PR protein may be identified by comparison of proteins isolated prior to, and at stages during and after, pathogen infection. PR proteins may also be identified by homology to known PR proteins, promoter analysis, or functional analysis of the expression products of a cDNA library. These techniques, together with other suitable techniques, would be known to a person of skill in the art.

For the purpose of the present invention, systemic activation of a gene may be defined as the activation of a gene prior to or during the systemic acquired resistance response of a plant to pathogen resistance. As discussed above, such genes will typically be expressed in uninfected areas of a plant, more typically throughout the plant, following the local response of a plant as a result of pathogen infection. Such genes usually encode products involved in the systemic acquired resistance of a plant to pathogen invasion, for example pathogenesis related proteins. Conversely, a gene which is substantially free of systemic activation will be under the control of a promoter which does not activate expression of the gene throughout the plant in uninfected tissues that are distant to the site of pathogen attack. Expression of such genes is limited to the site of infection or immediately adjacent to the site of infection. Promoters which are substantially free of systemic activated expression do not give rise to levels of expression throughout the plant prior to, during or after the systemic acquired resistance response, which are significantly above basal levels of expression, and do not give rise to expression throughout the plant that is a significant fraction of the expression levels attained locally in areas at or adjacent to sites of infection. Such basal levels may vary from plant to plant, although ideally should approach or be zero.

The cells of any particular plant will all contain the same genome, and thus behave according to the same rules. However, cells of a plant may exist in a variety of different states depending on the developmental pathway which they have followed. A number of genes are involved in the control of developmental choices made by plant cells. These genes, known as developmental control genes, are developmentally regulated, and typically expressed only in a particular plant tissue or organ at a specific stage of development. For example, a gene involved in the control of development of the flowering organs of a plant will only be expressed in those tissues from which flowering organs develop, prior to or during flowering. A gene which is substantially free of developmentally regulated expression may be defined as one which is not expressed only in a particular organ or tissue at a specific stage of development, or is expressed in such tissues at such times at a basal level only. Genes which are substantially free of developmentally regulated expression may be expressed in most tissues, throughout the life of the plant, for example those genes involved in food production, transport and storage. Other genes which are substantially free of developmentally regulated expression may be expressed only in response to external stimuli, such as environmental and chemical stimuli. Developmentally regulated genes and their promoters may be identified in a number of ways. For example, mutation analysis will allow the identification of mutations which prevent or inhibit the development of a particular organ or tissue of a plant, and thus the corresponding promoters and genes which must be involved in regulation of development. Such promoters and genes may also be identified from cDNA, genomic DNA or mRNA libraries, or by nucleotide or amino acid sequence homology to known developmentally regulated genes, or homology between the upstream regulatory sequences.

A promoter which is substantially free of developmentally regulated expression, in accordance with the present invention, may be identified in a number of ways. For example, mutation or deletion of a promoter which is substantially free of developmentally regulated expression will not result in inhibition or prevention of development, or disruption of the plant body plan.

Preferably, the recombinant or isolated DNA of the present invention encodes a promoter which is further substantially free of activation in response to environmental and hormonal stimuli, such as ABA, ethylene, oxidative and osmotic stresses and wounding. As a result, inappropriate expression in response to the above stimuli of a gene under control of the promoter of the invention is avoided. In this way, controlled expression of a gene is possible. Promoters which are substantially free of activation in response to environmental or hormonal stimuli may be identified by a number of ways, for example by linkage of the promoter sequence of interest to a reporter gene, transfection of a plant with the promoter-reporter gene construct, and analysis of the expression of the reporter gene following application of a hormonal or environmental stimuli. Promoters which do not activate expression of the reporter gene in response to the above stimuli, or cause low or basal levels of the reporter gene may be identified as being substantially free of chemical or environmental stimulation. Acceptable levels of low or basal levels will depend entirely on the gene being expressed. Thus, if the gene encodes an innocuous product, a low level of constitutive expression will be unlikely to impose a great metabolic burden on the plant. However, if the product is phytotoxic, even a low level of expression may be deleterious.

Preferably, the recombinant or isolated DNA of the invention encodes a promoter which is inducible in response to plant regulators. The plant regulators are preferably inducers of SAR, and may be natural or synthetic. Examples of such SAR inducers include salicylic acid (SA) and BTH (Novartis), and the analogues such as 4-chloro-SA, 5-chloro-SA and 3,5-chloro-SA, benzoic acid (BA), 2,3-dihydro-BA, dichloroisonicotinic acid (INA) and a number of halides of this compound (Sanchez-Casas & Klessig, *Plant Physiol.* 106 1675–1679 (1994); Conrath et al., *PNAS* 92 7143–7147 (1995)).

In the present invention, the gene encoding the 21.3 kDa pathogenesis related protein in *Asparagus officinalis* and equivalent proteins in the Lillaceae or Amaryllidaceae families will be referred to as the AoPRT-L gene. AoPRT-L shares a degree of homology with other PR proteins, particularly with those of the PR-5 family, such as tobacco osmotin and osmotin like protein. Several of the PR-5 family proteins have been characterized and some, for example osmotin, have been shown to exhibit local and systemic activation upon pathogen invasion and developmentally regulated expression. In contrast, the acidic PR-5 gene products appear to show local activation in response to pathogens. Very little information is available regarding the developmental expression of these genes, although evidence suggests that they, too, are developmentally regulated. For example, constitutive expression has been observed in non-embryonic tissue of the developing seed in maize (Malehorn et al., 1994 *Plant Physiol.*, 106: 1471–1481, and a thaumatin-like protein has been observed accumulating in ripening cherry fruits (Fils-Lycaon et al., 1996). The transcription profile of the AoPRT-L gene differs from these genes in that it is not activated in the systemic response to pathogen invasion, and exhibits minimal developmentally regulated expression. Further, unlike the PR-5 genes, AoPRT-L is not induced in response to a wide range of stimuli including ABA and ethylene. Salicylic acid and its synthetic analogue BTH both have the ability to induce expression from the AoPRT-L promoter.

The molecular weight of the AoPRT-L protein given herein is merely putative, and derived from the number of amino acids present in the protein. The 21.3 kDa protein encoded by the AoPRT-L gene has 223 amino acids. The molecular weights refer to the unmodified protein, and do not take account of any changes as a result of post-translational modifications.

The molecular weight given above refers only to that of the AoPRT-L gene of *Asparagus officinalis*. Those skilled in the art will be readily able to identify equivalent proteins from the Lillaceae or Amaryllidaceae families using standard methods known in the art. For example, genes encoding the proteins equivalent to AoPRT-L may be identified by nucleic acid hybridisation studies, Restriction Fragment Length Polymorphism mapping, PCR cloning, and other known methods. The AoPRT-L gene or fragments thereof may be used as a probe to identify genes or DNA sequences encoding equivalent proteins. A fragment of the AoPRT-L gene may be 10, 20, 30, 50, 75 or 100 nucleotides. Preferably, a fragment of 15 to 20 nucleotides is used as a probe. Typically, the probe will be used to hybridize to genes encoding equivalent proteins, under stringent conditions. Suitable conditions may be those given in Plant Genetic Transformation and Gene Expression: A Laboratory Manual, Ed. Draper, J et al, 1988, Blackwell Scientific Publications pp252–255 (which is hereby incorporated by reference), modified as follows: prehybridization, hybridization and washes at 55–65° C., final washes with 0.5×SSC, 0.1% SDS omitted.

Preferred promoters of the present invention are those which drive expression of the 21.3 kDa protein or equivalent proteins of the liliaceae or Amaryllidaceae families. The sequence of the *A. officinalis* promoter is shown in FIG. 6. It is envisaged that the whole promoter sequence shown in FIG. 6 may be used, or fragments thereof. The fragments may be 20, 50, 100 or 150 nucleotides in length. Such fragments are those which retain the characteristics of the native promoter sequence, namely being substantially free of systemically activated or developmentally regulated expression. Preferably, such fragments will also be inducible by SA or BTH. The isolation of the promoter sequences shown in the figures will be described in the Examples.

The promoter of the AoPRT-L gene from *Asparagus officinalis* may be isolated from a plant using techniques known in the art. For example, the promoter may be isolated by i) synthesizing cDNA from the mRNA isolated from cultured, mechanically isolated *Asparagus officinalis* cells, ii) differentially screening the cDNA to identify those clones induced upon adaptation to cell culture conditions, iii) isolating a differentially expressed cDNA encoding a gene of interest, iv) using this cDNA to probe genomic DNA of *Asparagus officinalis* for the sequence encoding the gene of interest v) identifying the upstream regulatory regions of the gene of interest, which includes the promoter of the gene. The promoters of equivalent proteins from the Lillaceae and Amaryllidaceae families, and promoters of proteins substantially homologous to the proteins of the first aspect of the invention may be identified using standard techniques known in the art. For example, the promoter may be isolated by i) synthesizing cDNA from mRNA of a plant cell of interest; ii) screening the cDNA library to identify clones showing the appropriate expression pattern; iii) isolating the cDNA clone of interest; iv) using this cDNA to isolate the gene by screening a genomic library;; v) identifying the upstream regulatory elements of the gene.

The techniques used in the above steps are known in the art. The isolation of viable cells from a plant according to step i) is described in International Patent Application WO 93/05164. Briefly, viable cells may be sheared from any monocotyledon or dicotyledon. Cells isolated in this manner from *Asparagus officinalis*, and placed in growth medium will dedifferentiate and initiate cell division when placed in cell culture. The adaptation to culture conditions results in the expression of a large number of genes which may not usually be expressed. Because the induction of cell division and dedifferentiation are features usually associated with wound response phenomena in dicots, it is envisaged that the promoters of the present invention isolated from the monocot *Asparagus officinalis* may be used to induce gene expression in either dicots or monocots.

The change in gene expression upon culturing of the mechanically isolated cells makes them a rich source of gene transcripts, and thus suitable for the production of a cDNA library. The construction and differential screening of a cDNA library is described in WO 93/05164.

Optionally, the suitability of promoters which hybridise to the above promoters of the present invention may be further assessed by functional analysis. Thus, favoured promoters which hybridise to the above promoters are those which do not show substantial systemic or developmentally regulated activation. Promoter sequences which hybridise under stringent conditions to whole or part of the promoter sequences of pAoPRT-L of *Asparagus officinalis*, equivalent proteins from the Lillaceae or Amarydillaceae families, or proteins substantially homologous thereto, are also included within the scope of this invention.

For identification of substantially homologous proteins or promoters, one can make use of specialist computer programmes. For instance one can make use of the default parameters of the GAP programme of the GCG package available on the SEQNET Computational Molecular Biology Facility at SERC, Daresbury, UK. This program provides "scores" for % identity and % similarity. Preferably, sequences having 60% or greater identity or 65% or greater similarity are included within the scope of the present invention. Thus, sequences having 70%, 80%, 90%, 95% or indeed 99% identity are included within the scope of the present invention. The skilled person will appreciate that these limits apply to both nucleic acid sequences and amino acid sequences (when one is identifying a protein analogous to the protein identified in the present invention, for instance). When considering sequences at the nucleic acid level, it is generally the case that identity/similarity of the coding sequence and/or promoter will be assessed.

Such promoter sequences may be identified by using standard techniques known in the art. For example, the pAoPRT-L promoter, or promoters of equivalent proteins from the Lillaceae or Amaryllidaceae families, or fragments thereof may be used as probes to identify promoters which will hybridise thereto. Typically, a suitable fragment will be 20, 30 or 40 nucleotides. Suitably stringent conditions are discussed above.

In a second aspect of the present invention there is provided a promoter comprising at least the SA responsive element from −247 bp to −132 bp of FIG. 6. In particular, chimeric promoters may be produced which have the desired expression characteristics of the native plant promoter, and the ability to induce expression in response to SA conferred by the presence of the SA responsible element of FIG. 6.

Such chimeric promoters may be produced using standard techniques or in recombinant DNA technology.

In a third aspect of the present invention, there is provided two or more inducible pathogenesis related protein promoter sequences according to the first aspect of the invention, arranged in series. The resulting promoter multimer may comprise a combination of any two or more of the preferred promoter sequences of the first aspect of the present invention. Any number of promoter sequences may be arranged in series to produce a multimer, depending upon any size and stability constraints of the expression system, and the desired level of gene expression. Preferably, the multimer comprises at least 2, at least 5, or, most preferably at least 7 promoter sequences. The promoter sequences of the multimer may linked directly to one another, or via intervening linking sequences. The intervening linking sequences may be of any suitable length to allow efficient functioning of the multimer, and be derived from foreign DNA. Preferably, the multimer includes at least one promoter sequence which comprises the minimal promoter −132 bp sequence shown in FIG. 6. Where only one of the two or more promoter sequences comprises the minimal −132 bp sequence shown in FIG. 6, it is preferable that this sequence is positioned closest to the gene to be expressed. In a most preferred embodiment of this aspect of the invention, there is provided a series of fragments of the promoter sequence shown in FIG. 6, operably linked to the minimal −132 bp promoter sequence of FIG. 6. In the most preferred embodiment, the fragments include the 247 to −132 bp SA responsive element.

In a fourth aspect of the present invention, there is provided an amplification system, comprising a pathogenesis-related protein promoter sequence according to the first aspect of the present invention. Preferably, the promoter of the present invention is operably linked to a transactivator sequence and a second promoter sequence, which is preferably the target of the transactivator sequence and is linked to DNA encoding the product of interest. Systems that can be used to amplify gene expression have been described in WO98/05789 and Moore et al., *PNAS* 95 379–381 (1997). Examples of amplification systems which do not involve transactivators include the mRNA viral replicase based system (Mori et al., *FEBS. Letters*, 336:171–174 (1993)), where the promoter of the present invention is operably linked to a viral replicase and a second gene, where the gene transcript is amplified by the replicase. The second gene may be anti-sense. Where the amplification system comprises a transactivator sequence, it is preferable for it to be placed downstream of the promoter sequence of the present invention, and the direction of the transcription of the promoter of this invention and the second promoter sequence to be in series or divergent. A preferred construct is shown in FIG. 16, although it will be appreciated by one of skill in the art that variations of such a construct are possible which will have the effect of amplifying expression from the promoter of the present invention. In the amplification construct of this aspect of the present invention, it is envisaged that the promoter according to the first aspect of the present invention will drive expression of the transactivator. The transactivator product may then initiate multiple rounds of transcription of the desired gene via the second promoter. In this way, there will be amplification of the initial signal which activated the pathogenesis-related protein promoter of the invention. Thus, an amplification construct may allow reduced amounts of activator substances such as SA or BTH to be used, while maintaining high expression of the desired gene. In a further embodiment, it is envisaged that the multimer according to the second aspect of the invention may comprise part of an amplification system.

Transactivator sequences are known in the art, and any suitable one may be used for the purpose of the present invention. The transactivator sequences may be natural or synthetic. In a preferred embodiment, the transactivator is LbG4, which consists of the mutated *E. coli* lac I gene fused to the transcriptional activator domain of Gal4 from yeast. The second promoter sequence may be any which is activatable by the transactivator. Where the transactivator is LhG4, the preferred promoter is pOP910. This is a minimal CaMV promoter with two rounds of binding sites for the LhG4 protein. Other transactivators include the Tet transactivator, in combination with the pTop10 promoter (Wienmann et al., *Plant Journal* 5 559–569 (1994)).

In a fifth aspect of the present invention, there is provided a promoter, multimer or amplification system according to the previous aspects operably linked to a DNA sequence encoding a product of interest. The DNA may encode a protein of interest, or a product able to regulate the production of a protein of interest. Proteins of interest include products sought to be harvested from a plant or plant cells in culture, products which may be expressed in the plant and alter the characteristics of the plant or plant cells in culture, products involved in the regulation of certain plant traits, and products such as marker genes. In particular, DNA encoding products which provide or enhance a beneficial feature of the transgenic plant are preferred. For example, the nucleic acid may encode proteins or antisense RNA transcripts in order to promote increased food values, higher yields, pest resistance, disease resistance, artificial male sterility (for example: barnase or PR-glucancase), female sterility, or flower and fruit ripening control. Representative nucleic acids of interest include for example, a bacterial dap A gene for increased lysine; Bt-endotoxin gene or protease inhibitor for insect resistance; lytic peptide genes for disease resistance, bacterial or plant EPSP for resistance to glyphospate herbicide (U.S. Pat. Nos. 4,940,835; 5,188,642; 4,971,908; 5,145,783; 5,312,910; 5,633,435, 5,627,061, 5,310,667; WO 9704103), bacterial or plant HPPD (WO9638567, WO9802562) for resistance to HPPD-inhibitors herbicides (for example diketole or isoxazoles), chitinase or glucan endo 1,3-B-glucosidase for fungicidal properties. Further, a DNA sequence may be introduced to act as a genetic tool to generate mutants or to assist in the identification, genetic tagging or isolation of genetic sequences. Examples of nucleic acids useful for modifying quality include: genes for starch biosynthesis or degrading enzymes (for example starcth synthases, starch branching enzymes) grain storage protein genes (for example sub-units protein of glutenin, gliadins or hordeins), or genes linked to the grain hardness.

The promoter-gene construct of the fifth aspect of the invention may further comprise a marker gene to allow monitoring of the expression of the heterologous DNA. Preferably, a marker gene is operably linked to the promoter, multimer or amplification system of the invention, in series with the heterologotis DNA encoding a product of interest. Induction of the promoter, multimer or amplification system will result in expression of the marker gene in the transformed cell or plant, thus enabling one to assess the level of induction of the product of interest easily without the need to harvest or destroy the whole or part of the plant, or culture of plant cells. Any suitable marker gene may be used. Examples include beta-glucuronidase, luciferase or green fluorescent protein.

The promoter-gene construct may also comprise additional regulatory sequences required for the efficient expression or targeting of the gene product. For example, 3' transcription regulation signals such as polyadenylation signals may be provided, as may any other regulatory sequence such as enhancers. Preferred 3' polyadenylation signals are derived from the Cauliflower Mosaic Virus 35S gene, although one skilled in the art would appreciate that other 3' polyadenylation signals could be used. The addition of a transit peptide sequence may be desired where the product is to be secreted from the cell.

The recombinant or isolated DNA according to any one of the aspects of the present invention may be in the form of a vector. The vector may be a plasmid, cosmid or phage. The vectors may be introduced directly into plant cells, using known methods in the art or may first be cloned in bacteria such as *E. coli*, before introduction into the plant cell. Where the vectors are to be cloned in microbial host cells, it is preferable that the vector further comprises one or more marker genes to enable the selection of transformed or transfected microbial cells harbouring the vector construct comprising the heterologous DNA. Sufficient start and stop signals, and regulatory sequences to allow expression of the heterologous DNA and/or marker gene in the microbial cell may also be included.

According to a sixth aspect of the present invention there is provided a host cell transfected or transformed with DNA described above. The host cell may be a plant cell or a microbial cell. The present invention also provides a transgenic plant cell culture, of a monocotyledon or dicotyledon, transformed with a promoter, multimer or amplification system of the present invention, preferably operably linked to a heterologous gene. Transformation methods are described below. The transgenic plant cell culture may be used to generate whole plants, and thus in a further aspect of the present invention there may be provided transgenic plants, seeds and propagating material, e.g. propagated shoots comprising DNA according to the invention. Preferred plants or parts or cells thereof for transformation include rice, maize, wheat, barley, sorghum, sugarcane, tobacco, rapeseed, sunflower, soybean, cotton, clover, and beans as well as sugar beet, potato, vegetables such as tomato, melon, cabbages, lettuce, carrot, beans, paprika and peppers.

The DNA of the present invention may be prepared using any convenient method involving coupling together successive nucleotides, and/or ligating oligo and/or polynucleotides, including in, vitro processes. Recombinant DNA technology remains the method of choice.

The DNA of the present invention may be introduced into plant cells using standard methods of the art. Preferably, DNA is transformed into plant cells using a disarmed Ti-plasmid vector and carried by *Agrobacterium,* by procedures known in the art. Alternatively, the foreign DNA may be introduced directly into plant cells using a microprojectile apparatus, or any other physical delivery system. The latter techniques are preferable where *Agrobacterium* is ineffective for stable transformation, for example in the transformation of cereal plant cells. Preferably, the transformation vector will comprise a cloning site or a multicloning site for the insertion of genes or other DNA (referred to herein as passenger genes) to be transferred to plant cells. The passenger genes or other DNA may be under the control of a promoter which differs in its expression characteristics from the promoter of the invention. For example, the passenger gene may be a marker gene under the control of a different promoter to that of the invention, such that when the construct is expressed in the plant, the marker gene may be expressed according to the characteristics of the promoter to which it linked, and not limited to the expression pattern of the promoter of the invention. Any suitable techniques which would allow for the stable incorporation of the DNA of the invention within the nuclear DNA of a plant cell would also be suitable.

In a seventh aspect of the present invention there is provided a method for the identification of agents capable of regulating the expression of heterologous genes which are operatively linked to the AoPRT-L promoter. The method may comprise the steps of applying a putative agent to a DNA sample comprising the AoPRT-L promoter operatively linked to a heterologous gene, measuring the expression level of the gene and comparing expression levels against a control system. This provides an indication of the ability of the agent to regulate gene expression via the AoPRT-L promoter. Putative agents of interest may be applied to a transformed plant, cell culture, tissue sample or in vitro system comprising the DNA sample. Agents of interest identified in this manner are preferably those which induce expression of a gene operatively linked to the AoPRT-L promoter.

The agent may be any natural or synthetic product, for example chemical compounds such as proteins, peptides, DNA or RNA sequences or hormones and analogues thereof. The heterologous gene to which the promoter is linked may be any gene, preferably one which expresses a quantifiable product. Preferred heterologous genes for this purpose include those which encode screenable markers, for example beta-glucuronidase or green fluorescent protein.

Agents identified by the above method may also be effective in regulating expression of the AoPRT-L gene itself or genes encoding pathogenesis related proteins equivalent or homologous to the AoPRT-L protein of *Asparagus officinalis*. The latter may include pathogenesis related proteins of the Lilliaceae or Amaryllidaceae family, or indeed of other plant families. Such agents may be effective at regulating or inducing a full or partial SAR response, thus rendering them useful as "crop protectants" for field use.

BRIEF DESCRIPTION OF THE INVENTION

The present invention will now be illustrated by the following Examples, which refer to the accompanying drawings, in which:

FIG. 1 shows the Nucleotide sequence of AoPRT-L cDNA (SEQ ID NO:2) together with the predicted amino-acid sequence of AoPRT-L (SEQ ID NO:3). The sequences and positions of binding of the primers used for IPCR (SEQ ID NO:4 and SEQ ID NO: 10, respectively) are indicated above the cDNA sequence and relevant enzyme restriction sites underlined.

FIG. 2 shows sequence homologies between AoPRT-L and other PR-5 proteins

FIG. 3 shows the accumulation of mRNA for AoPRT-L in Asparagus. FIG. 3(a) shows the induction of AoPRT-L expression following mechanical isolation of Asparagus cladode mesophyll cells. FIG. 3(b) shows the induction of AoPRT-L expression in chopped etiolated Asparagus seedlings and FIG. 3(c) shows the expression of AoPRT-L in SA-treated Asparagus.

FIG. 4 shows the expression of AoPRT-L mRNA following infection of Asparagus with *Stemphyllium versicarium*.

FIG. 5 shows a strategy for the isolation of the AoPRT-L promoter by IPCR.

Figure 6:
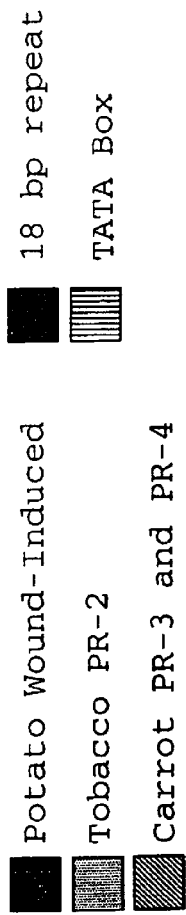

FIG. 6 shows the Nucleotide sequenc of the AoPRT-L promoter (SEQ ID NO:1). Sequences with homology to characterized promoter elements are boxes.

FIG. 7 shows the construction of AoPRT-L-GUS constructs.

Figure 8:
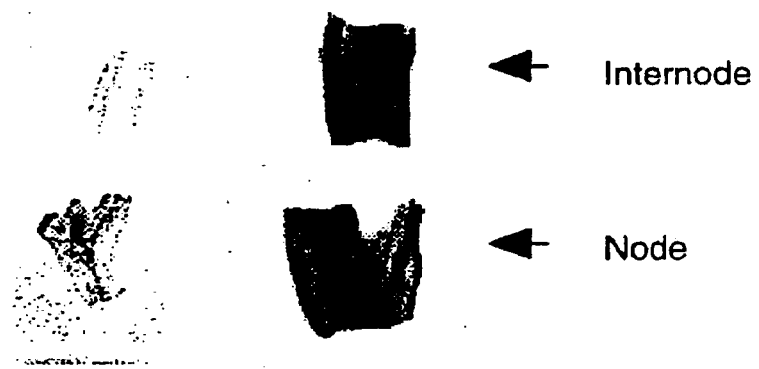

FIG. 8 shows the axial expression of AoPRT-L-GUS in transgenic tobacco compared with PR-1a-GUS.

FIG. 9 shows the expression of AoPRT-L-GUS in local and systemic tissues of transgenic tobacco infected with Tobacco Mosaic Virus (TMV) or *Pseudomonas syringae* pathovar *phaseolicola*. GUS activity was measured flurometricaily using the substance 4-methyl umbelliferone (4-MU) formed/minute/mg protein extract.

Figure 10:
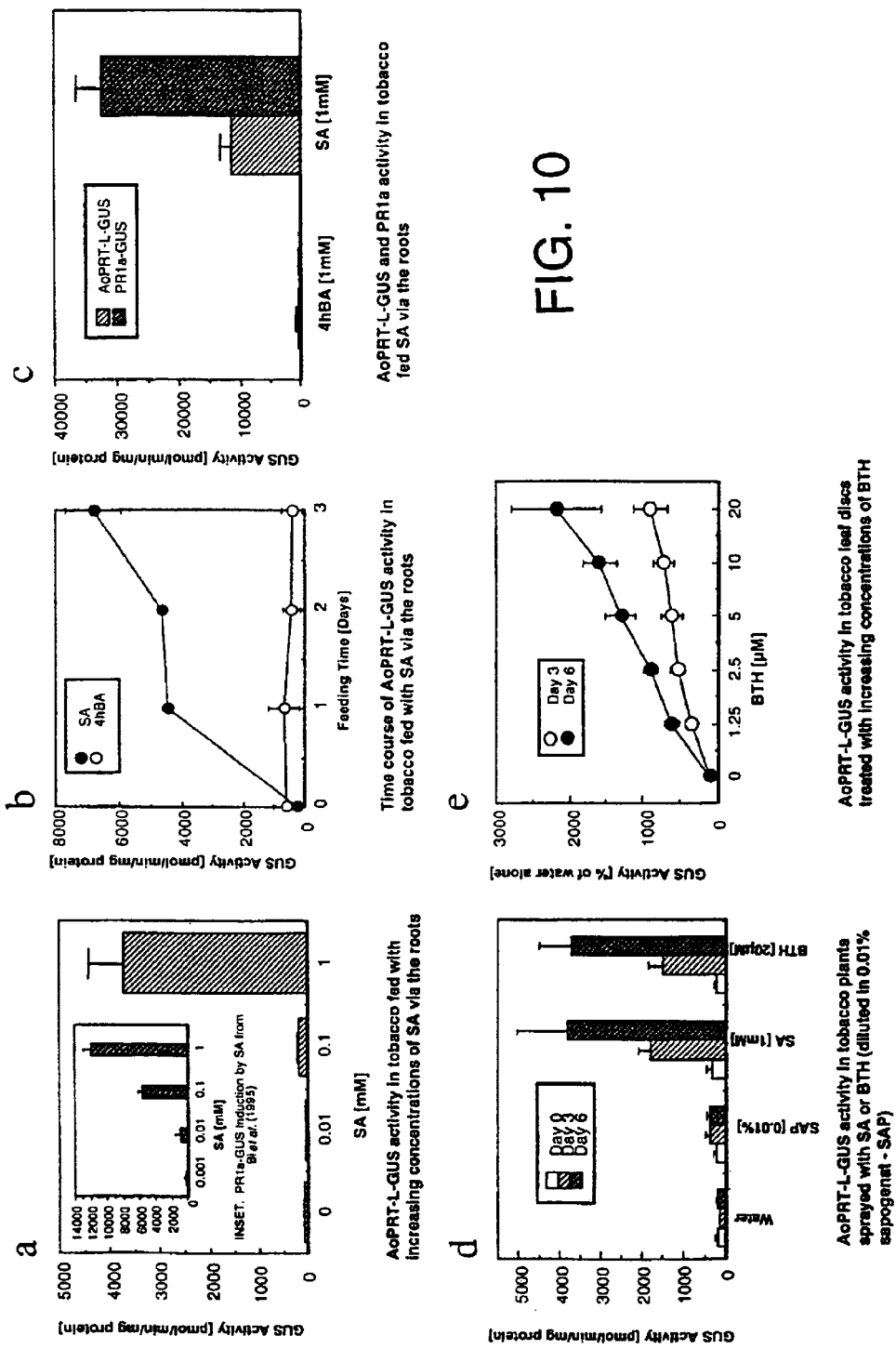

FIG. 10 shows the induction of AoPRT-L-GUS and PR-1a-GUS expression in transgenic tobacco treated with exogenous SA or BTH.

Figure 11:
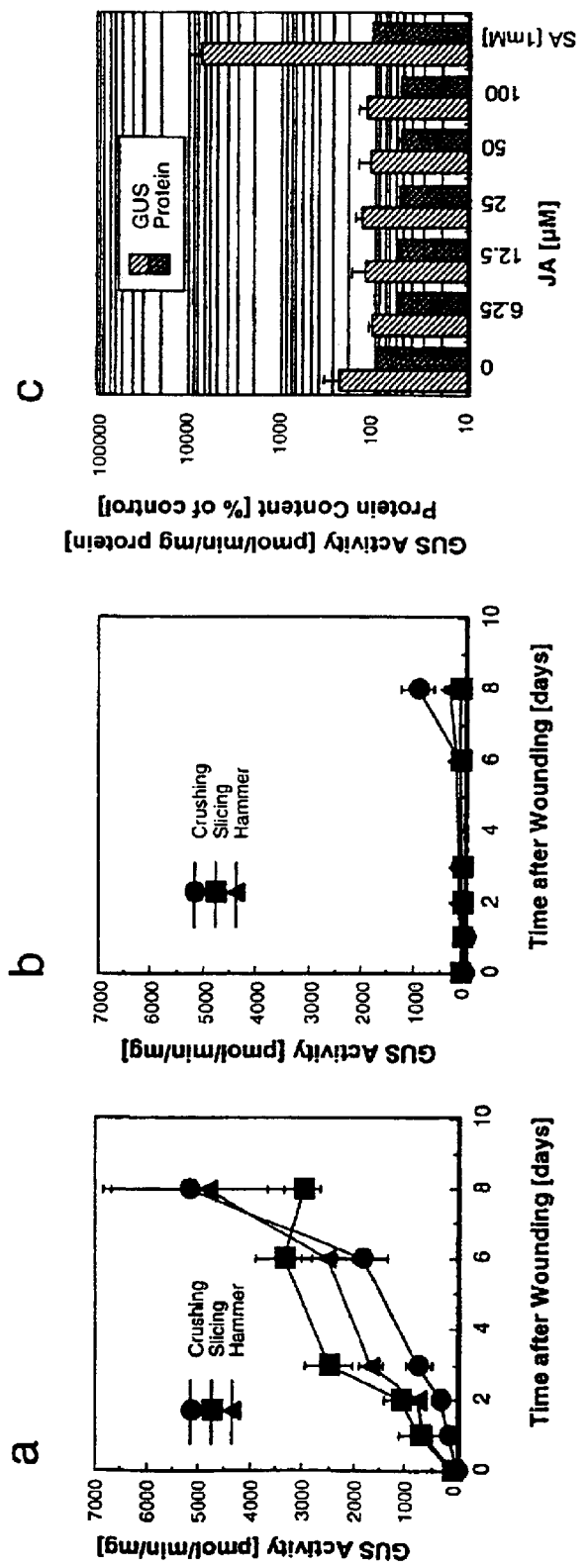

FIG. 11 shows the expression of (a) AoPR-1-GUS and (b) AoPRT-L-GUS in wounded transgenic tobacco, and (c) expression of AoPRT-L-GUS in transgenic tobacco leaf discs following treatment with exogenous jasmonate.

Figure 12:
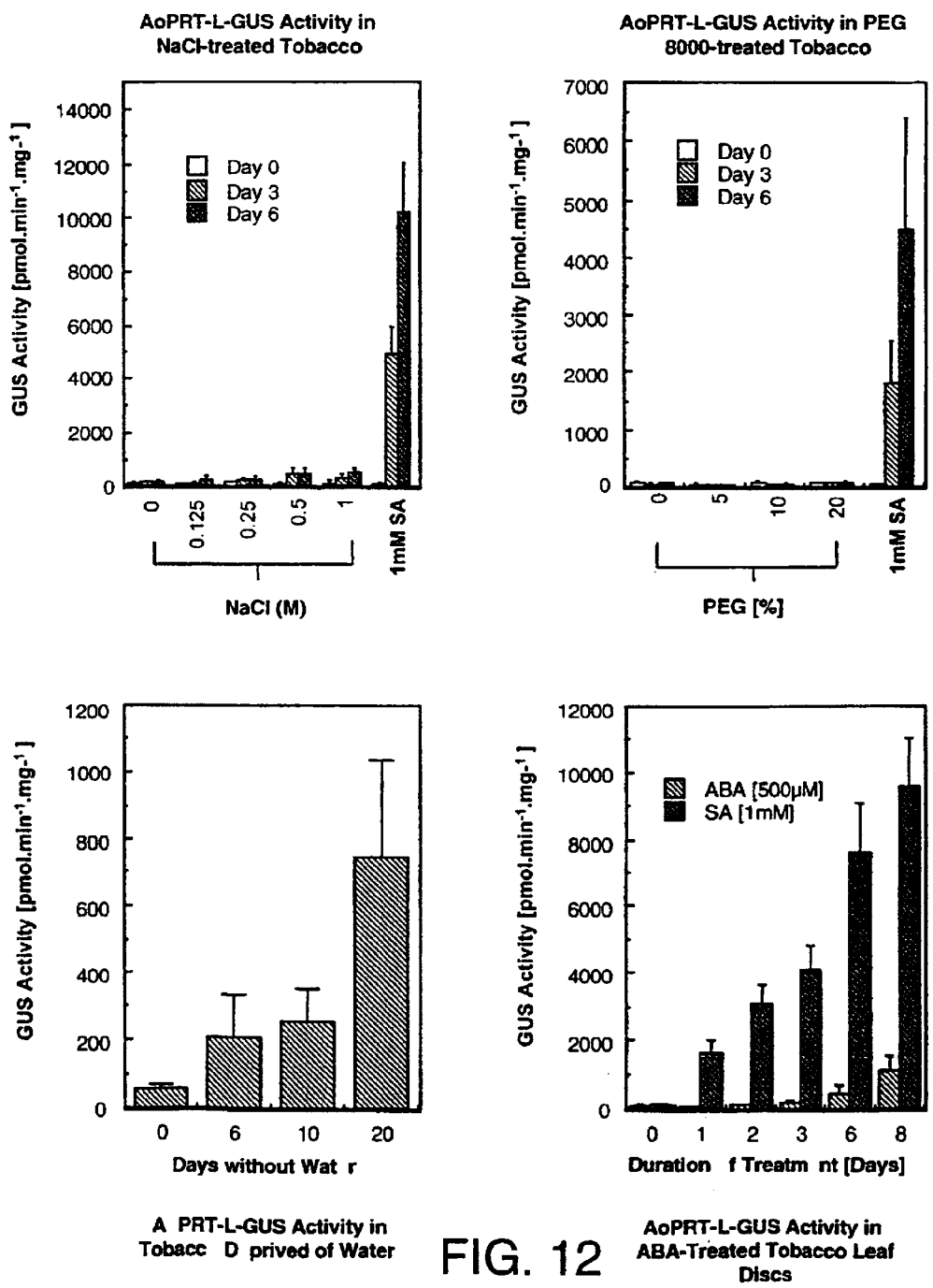

FIG. 12 shows the expression of AoPRT-L-GUS in leaves of transgenic tobacco root-fed with either NaCl or PEG 8000, subjected to water stress or leaf discs treated with ABA.

Figure 13:
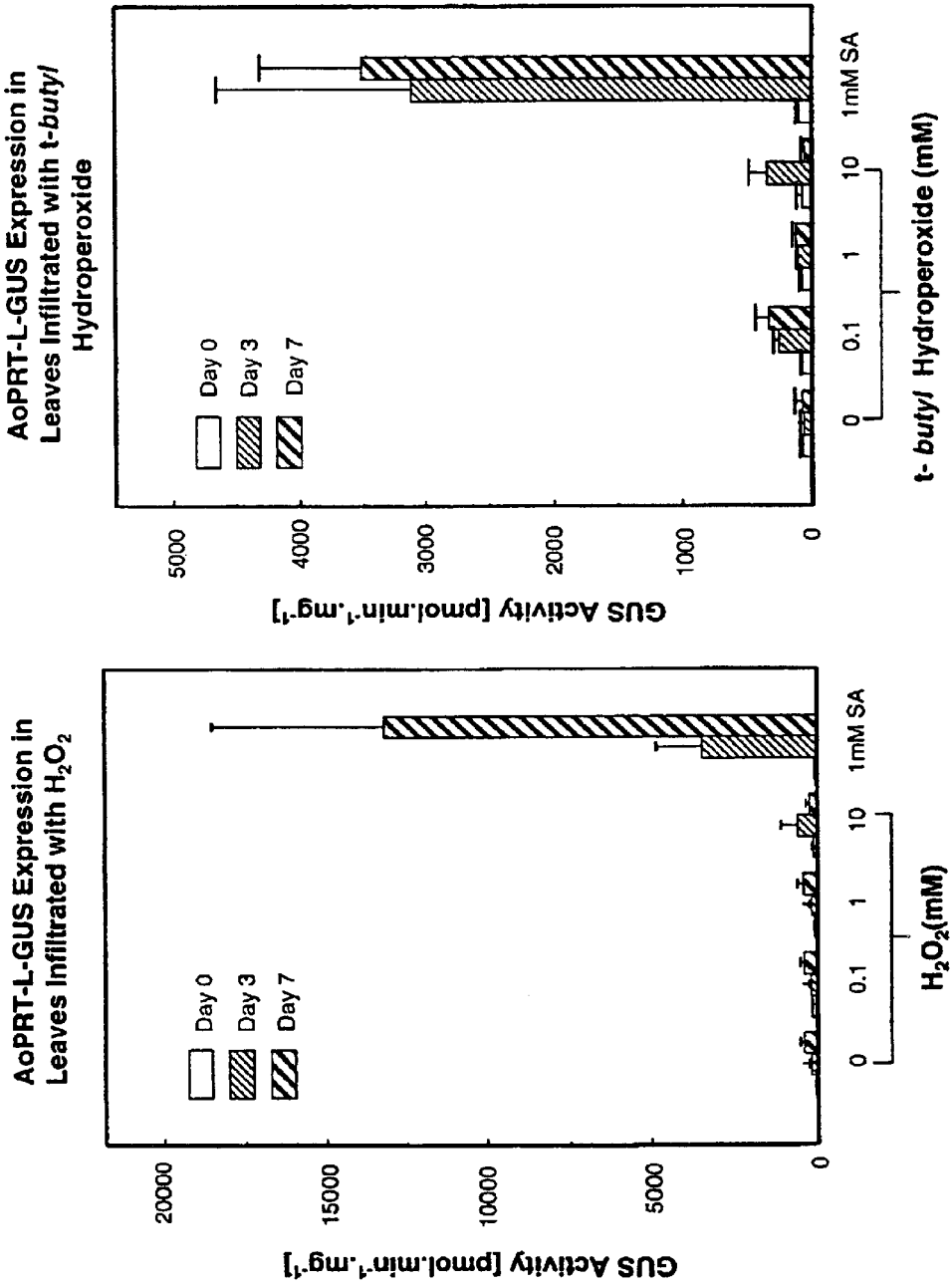

FIG. 13 shows the expression of AoPRT-L-GUS in transgenic tobacco leaves infiltrated with hydrogen peroxide or t-butyl hydroperoxide.

Figure 14:
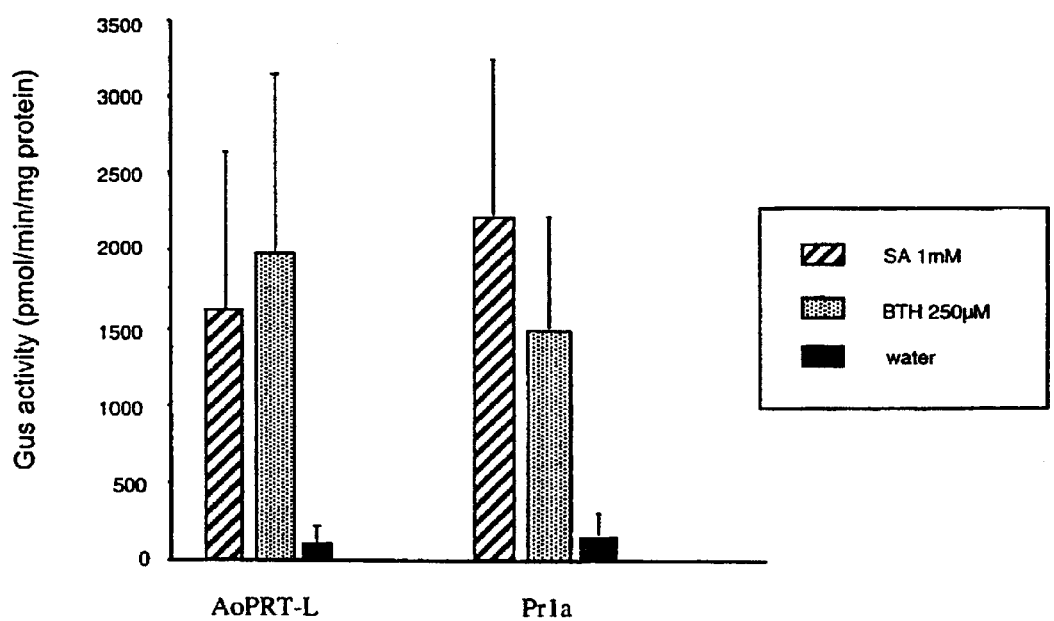

FIG. 14 shows the expression of AoPRT-L-GUS and PR1a-GUS in T0 transgenic *B. napus* leaf discs floated for 3 days on water, 1 mM SA or 250 μM BTH. Data are the average of 6 independent transformants/transgene.

Figure 15C:
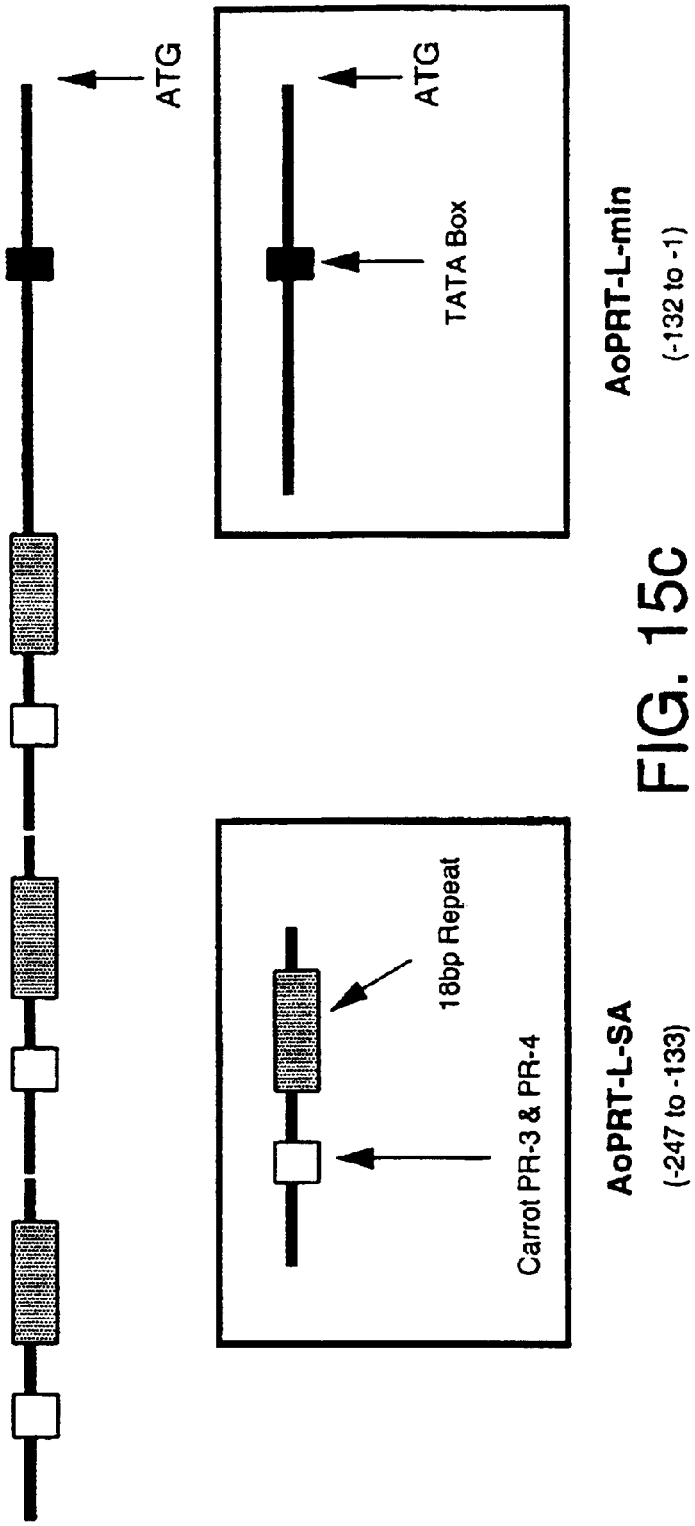

FIG. 15(a) is a diagrammatic representation of the AoPRT-L promoter deletions fused to the GUS reporter gene and FIG. 15(b) shows their response to exogenous SA in T0 transgenic tobacco. FIG. 15(c) is a diagrammatic representation showing arrangement of putative SA responsive elements in pMultAoPRT-L promoter.

Figure 16:
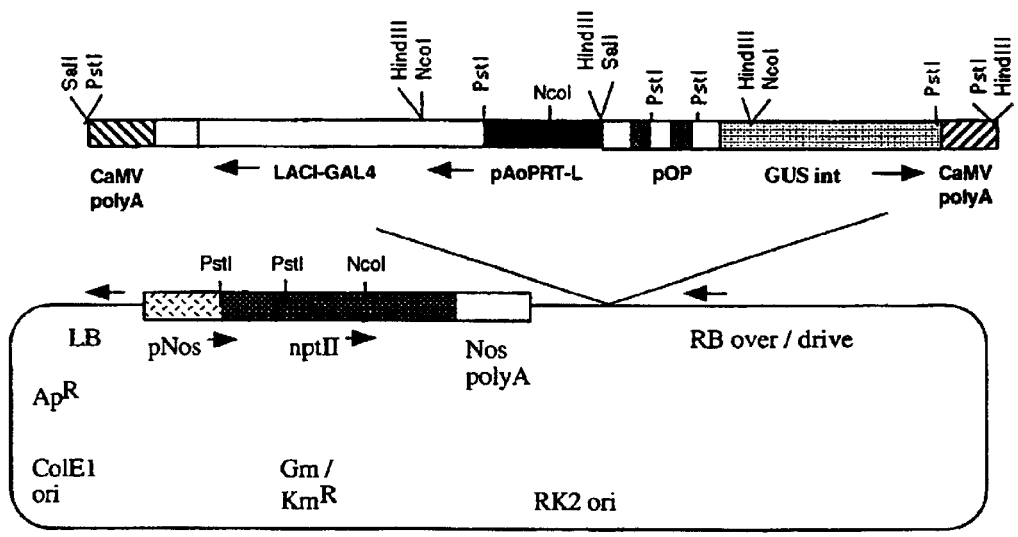

FIG. 16 is a diagrammatic representation of pAoPRT-L expression amplification construct pGB24.

In the examples, unless otherwise stated, all procedures for making and manipulating recombinant DNA were carried out using the standard techniques and protocols described in Sambrook J., Fritsch EF & Maniatis T et at., Molecular Cloning: A Laboratory Manual, 2nd Edition, Cold Spring Harbor Laboratory 1989.

EXAMPLES

Example 1

Isolation of an AoPRT-L cDNA and Characterisation of Expression of AoPRT-L in *Asparagus officinalis*

Single mesophyll cells isolated from *Asparagus officinalis* are capable of dedifferentiating and initiating cell division in an appropriate culture medium (Harikrishna et al., (1991) *J. Exp. Bol.* 42:791–799). Large changes in gene expression occur in these isolated cells during adaptation to cell culture conditions, thus mRNA isolated from these cells can be used to obtain genes specifically induced during this adaptation. Such genes include those upregulated by wounding and stress. The construction and screening of a cDNA library made from mechanically isolated *A. officinalis* cells is described previously (WO 93/05164; Warner et al.,. (1992) *Plant Molecular Biology* 19:555–561). One cDNA clone representing a differentially expressed mRNA was found to represent up to 0.2% of the cDNA library. DNA sequence analysis (FIG. 1) showed that the mRNA encodes a putative protein of predicted mass 21.3 kDa which is homologous to thaumatin-like genes (FIG. 2) and thus is a member of the PR5 gene family. Thus the gene was named AoPRT-L.

Analysis of the putative AoPRT-L protein sequence showed that it is most closely related to acidic secreted PR5 (a-PR5) proteins. The AoPRT-L gene product is recognised by a polyclonal antiserum raised against PR-5 and is secreted since it is found in the culture medium of Asparagus cells.

Northern hybridisation analysis using RNA isolated from mechanically isolated *A. officinalis* cells indicated that AoPRT-L is upregulated in mechanically isolated cladode cells (FIG. 3*a*). In chopped etiolated *A. officinalis* seedlings (<=0.5 cm in length) the AoPRT-L transcript was detectable from 3 days after wounding (FIG. 3*b*). However AoPRT-L does not behave like the wound inducible gene AoPR1 (WO 93/05164; Warner et al., (1992) Plant Molecular Biology 19:555–561) in that expression is not seen in sections of chopped etiolated seedlings greater than 0.5 cm in length and expression of AoPRT-L in sections of <=0.5 cm extends throughout the section and is not limited to the wound site (FIG. 3*b*).

AoPRT-L MRNA accumulation was observed following treatment with SA (FIG. 3*c*) and following infection with the fungal pathogen *Stemphyllium versicarium* (FIG. 4) but was not induced by the ethylene-generating compound ethephon.

Example 2

The Isolation of the Upstream Promoter Regions of the AoPRT-L Gene by the Inverse Polymerase Chain Reaction (IPCR)

An AoPRT-L promoter region was isolated from *A. officinalis* by the Inverse Polymerase Chain Reaction (IPCR) (FIG. 5). The technique was essentially as described in (WO 93/05164; Warner et al., (1993) Plant Journal 3:191–201).

*A. officinalis* genomic DNA was digested with EcoRI, religated to circularise the restriction fragments and PCR performed with the AoPRT-L specific primers of:

```
P1 5'-CGCGGAATTCGGTGTAGGTGCATTTGTTGG-3'(SEQ ID NO:9) (105-86 bp) and
       EcoRI
```

```
P2 5'-CGCCTGCAGCCAATCCTGGACCCTCACCG-3'(SEQ ID NO:10) (152-172 bp)
       PstI
```

A 0.8 kb DNA fragment was obtained that hybridised with the most 5' region of the AoPRT-L cDNA. This PCR product was cloned directly into the pCR 2.1 vector (Invitrogen) using the protocols supplied with Invitrogen's TA cloning kit. The resulting construct was named pIPCR-TA. DNA sequence analysis of the PCR product confirmed the authenticity of the fragment as containing the correct upstream promoter sequence (FIG. 6).

Examination of the AoPRT-L promoter sequence (FIG. 6) reveals regions of homology with other PR promoters have been identified including a tobacco PR-2 and carrot PR-3 and PR-4 like sequences. There also appears to be a c-myc consensus sequence at −344 to −339. However, the promoter contains no consensus G-box, PR-box or ABRE which suggests that pAoPRT-L will not be induced by ABA or ethylene.

Example 3

Construction of an AoPRT-L Promoter-GUS Chimeric Gene

The AoPRT-L promoter was obtained from pIPCR-TA by PCR using primers designed against both the 5'- and 3' ends of the promoter with extensions to provide appropriate restriction sites for further cloning:

```
5'-GGGTACCAAGCTTCTTATTGCGACCTGACTCTC 3'(SEQ ID NO:11)
    KpnI  HindIII
```

```
5'-CGCGGATCCGTCGACCTGCAGGATTGGTTGTGTGTTGTTTT 3'(SEQ ID NO:12)
      BamHI  SalI PstI
```

This PCR product was then digested with KpnI and PstI and ligated into the pJIT60 vector (identical to pJIT30 (Guerineau et al., (990) Plant Mol. Biol. 15, 127–136) but with a double rather than a single 35S CaMV promoter) digested with same enzymes. The result was named p22-JIT60. The sequence encoding the β-glucuronidase reporter enzyme containing an intron (GUS(INT) in pBluescript SK- (Firek et al., (1993) Plant Mol. Biol. 22: 129–142; Jefferson et al., (1987) EMBO J. 6:3901–3907; Vancanneyt et al., (1990) Mol. Gen. Genet 220: 245–250) was cloned into p22-JIT60, behind the AoPRT-L promoter sequence, by digesting with BamHI and EcoRI to give the construct p22-GUS(INT) JIT60. Finally the entire AoPRT-L promoter-GUS fragment was released from p22-GUS(INT) JIT60 using KpnI and XhoI and ligated into the binary vector pBIN19 (Bevan (1984) Nuc. Acids Res. 22: 8711–8721) which had been digested with KpnI and SalI to give p22-GUS(INT) Bin19 (FIG. 7).

The GUS gene is a convenient reporter gene whose expression can be monitored easily. It should be understood that in this and in the following examples GUS can be replaced by any gene of interest, to allow chemical-induction of the gene of interest.

Example 4

Developmental Expression of the AoPRT-L Promoter in Transgenic Tobacco

The AoPRT-L promoter construct (p22-GUS(INT) Bin 19) was transformed into *Nicotiana tabacum* (cv Samsun) using standard *Agrobacterium tumefaciens*-mediated transformation techniques (Draper et al., (1988): Plant Genetic Transformation and Gene Expression—A Laboratory Manual. Blackwell Scientific Publications, Oxford, UK). The expression of the GUS gene driven by the AoPRT-L promoter was analysed using assays described previously (Draper et al., (1988) supra).

Histochemical analysis demonstrated that, in untreated plants, AoPRT-L promoter-driven GUS is expressed only in sepals and at petiole-stem junctions (leaf axils) (FIG. 8). Additionally, histochemical staining of roots close to the crown (base of the stem) is occasionally observed. Thus the promoter exhibits minimal developmental activity in comparison to other published promoters.

Example 5
Non-Systemic Induction of AoPRT-L Promoter-driven GUS Expression in Pathogen-challenged Transgenic Tobacco AoPRT-L-GUS-transformed Samsun tobacco plants were infected with Tobacco Mosaic Virus (TMV) by abrading the surface of a single leaf with a mixture of virus and carborundum as previously described (Bi et al., (1995) Plant J. 8:235–245). TMV induces an N-gene-dependent hypersensitive response characterised by the appearance of lesions (areas of hypersensitive cell death) on the infected leaf. Inoculation of Samsun tobacco with TMV also induces SAR and the systemic accumulation of endogenous PR-1a (Bi et al., (1995), supra). At various time points after infection, leaf discs were cored from lesions (these cores also contained non-HR tissue directly abutting the lesion, from uninfected inter-lesion tissue on the same leaf and from a non-infected systemic leaf on the same plant). GUS activity in these discs was measured fluorimetrically. GUS activity was found to be elevated in the inoculated leaf in tissue undergoing HR (or tissue directly adjoining HR lesions) but not in inter-lesion or systemic tissue (FIG. 9).

Samsun tobacco plants harbouring the AoPRT-L promoter fusion with GUS were infected with *Pseudomonas syringae* pathovar *phaseolicola* ($2 \times 10^8$ per ml) by inoculation of the intercellular leaf spaces of a single leaf as previously described (Bi et al., (1995), supra). *Pseudomonas syringae* pathovar *phaseolicola* induces a non-host hypersensitive response at the site of infiltration. This treatment also induces systemic accumulation of endogenous PR-1 proteins (Bi el al., (1995), supra). At various time points after infection, leaf discs were cored from infected leaves and from non-infected systemic leaves on the same plant. Samples taken from infected leaves included samples from the infiltration site (destined to undergo, or undergoing, hypersensitive cell death) and from non-infiltrated tissue close to the inoculation site on the same leaf. GUS activity in these discs was measured. In this case GUS activity was only detected in samples taken from tissue adjacent to the HR lesion (FIG. 9). No activity was detected within the tissue undergoing HR or in systemic tissue. This suggests that it is the tissue surrounding TMV lesions rather than the lesion itself which accounts for the activity observed in TMV-infected tobacco. The higher activity observed following TMV infection is possibly due to the approximately 10-fold higher levels of SA observed following TMV challenge when compared to *Pseudomonas syringae* pathovar *phaseolicola*.

These data indicate that, unlike PR-1a, the AoPRT-L promoter is only activated in tissue close to hypersensitive response lesions and is not induced systemically.

Example 6
Induction of AoPRT-L Promoter-driven GUS Expression in SA- and BTH-treated Transgenic Tobacco AoPRT-L-GUS-transformed Samsun tobacco plants were root-fed with increasing concentrations of SA for 3 days after which time leaf cores were taken and GUS activity was measured flurometrically. Substantial induction of the AoPRT-L promoter-GUS fusion was observed at 1 mM SA, with little induction at 0.1 mM SA (FIG. 10a). Thus, the AoPRT-L promoter-GUS fusion is an order of magnitude less sensitive to SA than PR-1a-GUS which is clearly induced at 10–100 $\mu$M SA (Bi et al., (1995), supra; Mur et al., (1996) Plant J. 9:559–571). Treatment with 1 mM SA showed a clear time-dependent induction of the AoPRT-L promoter-GUS fusion compared to the inactive SA analogue 4-hydroxybenzoic acid (4hBA), observable 1 day after treatment commenced. (FIG. 10b). SA induction of AoPRT-L-GUS-transformed plants gives about ⅓ of the GUS activity seen in pPR-1a-GUS-transformed tobacco. (FIG. 10c).

AoPRT-L-GUS-transformed Samsun tobacco plants were sprayed with 1 mM SA or 20 $\mu$M BTH (applied in a 0.01% sapogenat solution used as a wetting agent). Plants were sprayed once, allowed to dry and then sprayed again on the same day (day 0). After 3 or 6 days leaf cores were taken and GUS activity was measured using a standard fluorimetric assay. BTH proved to be as effective an inducer of GUS expression driven by the AoPRT-L promoter as was SA (FIG. 10d). Leaf cores from tobacco harbouring the AoPRT-L promoter fusion with GUS were floated for 3 or 6 days on water containing increasing concentrations of BTH after which time GUS activity in the leaf discs was measured fluorometrically. BTH-induced GUS activity is observed with the use of 1.25 $\mu$M BTH (FIG. 10e).

These data indicate:
1) the AoPRT-L promoter-GUS fusion is inducible by SA in transgenic tobacco.
2) That the AoPRT-L promoter-GUS fusion is an order of magnitude less sensitive to SA concentration, and shows approximately ⅓ of the induction compared to a PR-1a promoter-GUS construct.
3) BTH is an effective inducer of the AoPRT-L promoter-GUS fusion when applied as a foliar spray or in vitro.

Example 7
Wounding or the Wound Signal Jasmonic Acid, ABA and Osmotic Stress Fail to Induce AoPRT-L Promoter-driven GUS Expression in Transgenic Tobacco Tobacco plants harbouring either the AoPRT-L promoter fusion with GUS or an AoPR-1-GUS construct were wounded by one of 3 methods. The leaf lamina was either crushed with forceps, sliced with scissors or subjected to a combination of crushing and puncturing by striking the leaf with a meat tenderising mallet (hammer). After 1, 2, 3, 6 or 8 days leaf cores were taken from the damaged tissue and GUS activity measured. AoPR-1 is a wound-induced gene expressed at wound sites in chopped etiolated *A. officinalis* seedlings. The AoPR-1 promoter-GUS construct is also wound-inducible when introduced into tobacco (Warner et al., (1994) Plant J. 6:31–43; Mur et al., (1996) Plant J. 9:559–571). AoPR-1 promoter-driven GUS activity is elevated by all 3 wounding treatments with enhanced GUS activity observable at 1–2 days following treatment (FIG. 11a). In contrast, no increase in AoPRT-L promoter-driven GUS expression was observed with any wounding treatment with the exception of a modest increase at day 8 following crushing with forceps which is likely not to be due to wounding since at this stage the tissue is extremely desiccated (FIG. 11b).

Wounding of tobacco leaves (using the hammer method) or infection of tobacco with *Pseudomonas syringae* pathovar *phaseolicola* induces local accumulation of the wound-related phytohormone jasmonic acid (JA) (Kenton et al., submitted; Mur et al., (1997) Trends in Microbiol 5:297–300). Leaf cores from tobacco harbouring the AoPRT-L promoter fusion with GUS were floated for 3 days on water containing increasing concentrations of JA after which time GUS activity in the leaf discs was measured using a standard fluorimetric assay. Compared with flotation on 1 mM SA, JA failed to induce any increase in AoPRT-L promoter-driven GUS activity at any concentration tested (FIG. 11c).

These data indicate that, compared to expression of a wound-inducible promoter-GUS fusion (AoPR-1 promoter-GUS), the AoPRT-L promoter-GUS construct is essentially insensitive to mechanical damage. In addition, the AoPRT-L promoter-GUS is not induced by the known wound signal JA and by ethylene.

Example 8

Salt and Water Stresses, and the Water Stress-related Hormone Abscisic Acid (ABA) Fail to Induce Substantial Expression of AoPRT-L-promoter-GUS Activity in Transgenic Tobacco Since AoPRT-L belongs to class 5 family of PR proteins which also contains drought-induced genes such as those encoding osmotins, the response to a number of water-related stresses was examined. Neither a high concentration of salt or 20% PEG 8000, both of which induce expression of osmotin or osmotin-like genes in several species, induced expression of the AoPRT-L-promoter-GUS construct in transgenic tobacco (FIGS. 12a and 12b). A slight increase in expression was observed when water was withheld for 20 days from tobacco harbouring the AoPRT-L-promoter-GUS construct, by which time the plants were severely wilted (FIG. 12c). Similarly, a high concentration of ABA induced a slight increase in AoPRT-L-promoter-GUS in leaf discs of transgenic tobacco (FIG. 12d). Two points should be emphasised. 1) The level of drought or ABA induction is typically an order of magnitude lower than that observed using SA. 2) Both dehydration and ABA treatment induce substantial protein loss in tobacco, thus the apparent increase in GUS activity may be an artefact of differential sensitivity of GUS (compared with some other major leaf proteins) to the mechanism of protein loss.

These data suggest that the AoPRT-L promoter is substantially insensitive to water-related stresses and that any low-level expression which might occur is likely only in severely damaged plants.

Example 9

The AoPRT-L Promoter-GUS Construct is Insensitive to Pro-oxidants

The observation that AoPRT-L promoter-driven GUS activity is elevated in tissue close to the site of pathogen challenge suggests a role for SA as a causal agent of induction. However, the production of reactive oxygen species (ROS) during plant-pathogen interactions has received considerable interest in recent years. Briefly, recognition of a pathogen results in the production of a burst of $H_2O_2$. Currently the most popular model for this 'oxidative burst' is that $H_2O_2$ derives from the dismutation of superoxide produced by a cell-surface NADPH oxidase. Several defence-related genes (including AoPR1) are directly sensitive to $H_2O_2$ (Bi et al., (1995) supra). In addition, high levels of $H_2O_2$ are capable of inducing SA synthesis (Neuenschwander et al., (1995) *Plant Journal* 8:227–233; Summermatter et al., (1995) *Plant Physiology* 108:1379–1385). Finally, ROS accumulation is also a feature of chilling, ozone and UV stress and elevated ROS levels are also found in senescent tissue.

In order to test whether oxidative stress is likely to induce high levels of AoPRT-L promoter-driven gene expression, $H_2O_2$ was infiltrated into leaf panels of transgenic tobacco harbouring the AoPRT-L-promoter-GUS construct (FIG. 13a). The concentrations of $H_2O_2$ used have been shown to induce AoPR1-GUS expression in tobacco (Bi et al., (1995)—see Example 5). $H_2O_2$ failed to induce AoPRT-L-promoter-GUS expression over the concentration range tested. However, $H_2O_2$ has a limited half-life (around 10 mins—Levine et al., (1994) *Cell* 79: 583–593) in the apoplast, thus the experiment was repeated using a stable peroxide, t-butyl-hydroperoxide (FIG. 13b). Again, no GUS expression was detected despite the severe visible tissue damage which occurred at higher concentrations of t-butyl-hydroperoxide (in contrast to $H_2O_2$ which produced no visible symptoms).

These data suggest that, unlike PR-1a (Bi et al., (1995)—see Example 5; Neuenschwander et al., (1995) *Plant Journal* 8: 227–233), AoPRT-L promoter-driven gene expression is unlikely to be encountered even under conditions of high ROS stress or in the presence of ROS-mediated tissue damage.

Example 10

The AoPRT-L Promoter Is Induced by SA and BTH in *Brassica napus*

The AoPRT-L-GUS fusion in pJIT60-P22 GUS-int was transferred as a SstI-XhoI fragment into SstI, SalI-cut pTZ19 (Pharmacia) forming pGB4. The AoPRT-L-GUS gene was then cloned as a HindIII fragment into the HindIII site of the binary vector SCV-nos nptII (WO 96/30529) forming pGB4-SCV, in which the direction of transcription of AoPRT-L is the same as that of the nptII gene. pGB4-SCV was transferred to the agrobacterial strain pGV2260 and transformed *B. napus* plants produced by agrobacterial transformation essentially as described in Moloney et al., (1989) *Plant Cell Reports* 8: 238–242. Transformed plants exhibited similar levels of GUS activity when treated with 1 mM SA or 250 $\mu$M BTH (FIG. 14). AoPRT-L-GUS and PR1a plants also exhibited similar levels of GUS activity on SA or BTH induction (FIG. 14)

Example 11

The AoPRT-L Promoter Is Induced by SA and BTH in *Zea mays*

Maize plants containing AoPRT-L-GUS were produced by biolistic transformation of callus material with pJIT60-P22 GUS int. The transformed plants exhibited GUS activity when treated with SA or BTH.

Example 12

Identification and Multimerisation of an SA/BTH Responsive Element in the AoPRT-L Promoter A series of 3 AoPRT-L 5' promoter deletion—Gus fusion constructs were constructed using the following primers designed to regions of the AoPRT-L promoter (FIG. 15a):

```
5'GCGAAGCTTCCATGTCATGAGAGAAGCAC 3'(-361 bp) (SEQ ID NO:13)
    HindIII

5'GCGAAGCTTTTGGAAACTGAATACCTACA 3'(-247 bp) (SEQ ID NO:14)
    HindIII

5'GCGAAGCTTACAAAGGCTTAGACTTTCCA 3'(-132 bp) (SEQ ID NO:15)
    HindIII
```

Each of the above primers, in conjunction with the primer below, was used in a PCR reaction with p22-JIT60 as template:

```
5'GGGATCCGTCGACCTGCAGATTGGTTGTGTGTTGTTTTTG 3'(SEQ ID NO:16)
    BamHI  SalI   PstI
```

The PCR products were cloned as HindIII, BamHI fragments into HindIII, BamHI-cut p22-GUS (INT) JIT60. The resulting pAoPRT-L-GUS-CaMV polyA chimeric genes were cloned as KpnI, XhoI fragments into KpnI, SalI—cut pBin19 and transformed into Samsun tobacco. The GUS activity of transformants was measured after induction of leaf discs with 1 mM SA. A significant reduction of activity was observed after deletion of up to −132 bp (FIG. 15b). Thus the SA responsive element lies between −247 bp and the putative CAT (−50–47) and TATA box at −64 to −57 bp.

In order to construct an AoPRT-L promoter that has higher expression, the region −247 bp to −133 bp was amplified from p22-JIT60 and placed twice in front of a −247 bp AoPRT-L promoter. This AoPRT-Lx3 promoter was constructed as follows: The primers below were used to PCR the 0 bp to −247 bp AoPRT-L promoter from p22-JIT60.

```
5'-TCTAGGTACCCTTTGCGTGGTCGACTTGGAAACTGAATACCTAC-3'(SEQ ID NO:17)
      KpnI           SalI

5'GGGATCCGTCGACCTGCAGATTGGTTGTGTGTTGTTTTTG 3'(SEQ ID NO:16)
    BamHI  SalI   PstI
```

This was cloned as a KpnI, PstI fragment into pUC19. The 133 bp to −247 bp pAoPRT-L region was amplified with the primers:

```
5'TCTAGGTACCCTTTGCGTGGTCGACTTGGAAACTGAATACCTAC 3'(SEQ ID NO:18)
    KpnI           SalI

5'GAAAGTCTAAGCCTCGAGGGAATAAGGTACGAGTTCGTGGAC 3'(SEQ ID NO:19)
           XhoI
```

This fragment was cloned as a KpnI, XhoI fragment between the KpnI and SalI sites of the pUC19-derived plasmid forming pAoPRT-Lx2. The −133 bp to −247 bp pAoPRT-L fragment was then cloned as a KpnI, XhoI fragment between the KpnI and SalI sites of pAoPRT-Lx2 forming pAoPRT-Lx3 (FIG. 15c). Next the AoPRT-Lx3 promoter was cloned as an KpnI, PstI fragment into KpnI, PstI-cut p22-JIT60 forming pAoPRT-Lx3-JIT60. The pAoPRT-Lx3 was transferred from pAoPRT-L-x-JIT60 as a KpnI, BamHI fragment into KpnI, BamHI-cut p22-GUS (INT) JIT 60. Finally the resulting pAoPRT-Lx3 -GUS-CaMV poly A chimeric gene was cloned as KpnI, XhoI fragments into KpnI, SalI-cut pBin19 and transformed into samsun tobacco. The resulting plants exhibit a significantly greater level of GUS activity on SA or BTH induction than the equivalent AoPRT-L-GUS plants.

Example 13

Amplification of Expression of the AoPRT-L Promoter by the Use of a Transactivating System A way of increasing the activity of the AoPRT-L promoter whilst retaining tight regulation of the promoter is to use a system that will amplify expression of the AoPRT-L promoter. An amplification system was built using a transactivator (described in WO98/05789 and Moore et al., (1997) Proc. Natl. Acad. Sci. USA. 95, 379–381). The AoPRT-L promoter is linked to a synthetic transactivator (LhG4) and the target promoter of the transactivator (pOP) to the gene to be expressed. LhG4 consists of a mutated E. coli lacI gene fused to the transcriptional activator domain of the GAL4 from yeast. pOP910 is a minimal 35S CaMV promoter with two binding sites for the LhG4 protein. Since the transactivator can initiate multiple rounds of transcription from pOP, there is amplification of the initial signal that activated the AoPRT-L promoter.

The amplification system was constructed by the following steps. The pOP910 promoter was excised from pX-910TAG (K. Palme, Max Planck Institut fur Zuchtungsforchung, Koln, Germany) as a SstI-NcoI fragment and cloned into SstI,NcoI-cut pDH68 (pDH68 consists of a Pea Plastocyanin promoter (Pwee and Gray (1993) Plant J. 3, 437–449) linked to an intron GUS gene (D. Twell, Leicester University) cloned between the SstI and EcoRI sites of the vector pJIT30 (Guerineau et al., (1990) Plant Mol. Biol. 15, 127–136)). The resulting pOP-GUS int-CaMV polyA chimeric gene was transferred as a SstI (rendered blunt), XhoI fragment into the EcoRV, XhoI-cut cloning vector pIC19H (Marsh et al., (1984) Gene 32, 481–485). From this plasmid the chimeric gene was recovered as a SalI, XhoI fragment and cloned into SalI-cut pNos nptII-SCV forming pWP320-SCVA. To construct a fusion of pAoPRT-L to LhG4 the AoPRT-L promoter was first transferred as an HindIII, PstI fragment from pGB4 into HindIII, PstI-cut pBluescript KS+forming pGB21. pGALA (I, Moore, University of Oxford, UK) contains the LhG4 gene linked to a CaMV poly A terminator. This gene was excised as a KpnI, PstI fragment and cloned between the KpnI and PstI sites of the vector pT7Blue2 (Novagen) forming pGB22 The Kpn (rendered blunt), NotI fragment of pGB22 was then cloned into the SmaI, NotI sites of pGB21 forming pGB23. The resulting pAoPRT-L-LhG4 fusion was transferred as an Sal fragment into SalI-cut pWP320-SCVA forming pGB24 (FIG. 16).

Tobacco and *B. napits* plants containing the pGB24 T-DNA region exhibit a significantly greater level of GUS activity on SA or BTH induction than equivalent AoPRT-L-GUS plants.

What is claimed is:

1. A recombinant or isolated DNA molecule comprising an inducible pathogenesis-related protein gene promoter wherein said promoter is a nucleic acid molecule having SEQ ID NO:1 that naturally drives the expression of a 21.3 kDa protein in *Asparagus officinalis*.

2. The recombinant or isolated DNA molecule of claim 1 operably linked to a DNA sequence encoding a product of interest.

3. The recombinant or isolated DNA molecule of claim 2, wherein said product of interest is a protein, or a product which is able to regulate expression of a protein.

4. The recombinant or isolated DNA molecule of claim 2 wherein said product, when expressed, affects a plant trait.

5. The recombinant or isolated DNA molecule of claim 4, wherein the plant trait affected is any one of pathogen resistance, disease control, sterility, fertility or fruit ripening.

6. The recombinant or isolated DNA molecule of claim 2 further comprising a marker gene.

7. A vector comprising the recombinant or isolated DNA molecule of claim 1.

8. A host cell comprising the vector of claim 7.

9. The host cell of claim 8, wherein said host cell is a plant cell or a microbial cell.

10. A transgenic plant comprising at least one plant cell of claim 9.

11. A method of identifying an agent capable of regulating the expression of a heterologous gene which is operatively linked to a recombinant or isolated DNA molecule comprising an inducible pathogenesis-related protein gene promoter wherein said promoter is chosen from the group consisting of:

i) a nucleic acid molecule having SEQ ID NO:1 that naturally drives the expression of a 21.3 k Da protein in *Asparagus officinalis*, ii) a nucleic acid molecule having a sequence 90% identical to SEQ ID NO:1, wherein said molecule is a promoter, whose expression is
a) induced by salicylic acid (SA) and by BTH (benzo(1, 2,3) thiadiazole-7-carbothoic acid S methyl ester), b) is not systemically activated by pathogen infection, and c) exhibits minimal developmentally-regulated expression;

iii) a nucleic acid molecule that hybridizes under stringent conditions to any one of the molecules of i) or ii), wherein said molecule acts as an inducible promoter, whose expression is induced by SA and by BTH, is not systemically activated by pathogen infection, and exhibits minimal developmentally-regulated expression; and iv) a fragment of at least 100 nucleotides of the nucleic acid molecule of i) wherein said fragment acts as an inducible promoter, whose expression is a) induced by SA and by BTH, b) is not systemically activated by pathogen infection, and c) exhibits minimal developmentally-regulated expression, the method comprising applying a putative agent to a sample comprising the promoter operatively linked to a gene, and measuring the expression level of the heterologous gene.

12. A recombinant or isolated DNA molecule comprising at least two promoter sequences of claim 1 arranged in series.

13. The recombinant or isolated DNA molecule of claim 12 further comprising linker sequences between said promoter sequences.

14. A recombinant or isolated DNA molecule comprising a promoter of claim 1, operably linked to a transactivator sequence and a second promoter sequence.

15. The recombinant or isolated DNA molecule of claim 14, wherein said second promoter sequence is the target of said transactivator sequence.

16. A recombinant or isolated DNA molecule comprising a promoter of claim 1 operably linked to a mRNA viral replicase system.

17. The recombinant or isolated DNA molecule of claim 14 or 15, wherein said transactivator sequence is a mutated *E. coli* lacI gene fused to the transcriptional activator domain of the GAL4 from yeast (yielding LhG4 protein), and said second promoter sequence is a minimal 35S CaMV promoter with two binding sites for said LhG4 protein.

* * * * *